(12) United States Patent
Du et al.

(10) Patent No.: US 11,485,977 B2
(45) Date of Patent: Nov. 1, 2022

(54) METHODS AND SYSTEMS FOR AUTOINDUCTION OF PROTEIN EXPRESSION

(71) Applicant: Adagene Inc., Cayman Islands (GB)

(72) Inventors: Fangyong Du, New Haven, CT (US); Peter Peizhi Luo, Lansdale, PA (US)

(73) Assignee: ADAGENE, INC., Grand Cayman (KY)

( * ) Notice: Subject to any disclaimer, the term of this patent is extended or adjusted under 35 U.S.C. 154(b) by 0 days.

(21) Appl. No.: 15/536,939

(22) PCT Filed: Dec. 19, 2014

(86) PCT No.: PCT/CN2014/094388
§ 371 (c)(1),
(2) Date: Jun. 16, 2017

(87) PCT Pub. No.: WO2016/095211
PCT Pub. Date: Jun. 23, 2016

(65) Prior Publication Data
US 2019/0062760 A1    Feb. 28, 2019

(51) Int. Cl.
*C12N 15/63*     (2006.01)
*C07K 16/06*     (2006.01)
*C12N 15/72*     (2006.01)
*C12N 15/73*     (2006.01)

(52) U.S. Cl.
CPC ............ *C12N 15/635* (2013.01); *C07K 16/06* (2013.01); *C12N 15/63* (2013.01); *C12N 15/72* (2013.01); *C12N 15/73* (2013.01); *C07K 2317/14* (2013.01); *C07K 2317/55* (2013.01)

(58) Field of Classification Search
CPC ...... C12N 15/72; C12N 15/635; C12N 15/63; C12N 15/73; C07K 16/06; C07K 2317/14; C07K 2317/55
See application file for complete search history.

(56) References Cited

U.S. PATENT DOCUMENTS

| | | | |
|---|---|---|---|
| 5,173,418 A | 12/1992 | Molin et al. | |
| 2004/0180423 A1 | 9/2004 | Studier | |
| 2005/0287669 A1* | 12/2005 | Chao | C07K 14/805 435/455 |
| 2007/0212782 A1 | 9/2007 | Studier | |
| 2010/0113304 A1* | 5/2010 | Hufton | C12N 15/1037 506/14 |
| 2010/0184157 A1* | 7/2010 | Williams | C12N 15/64 435/91.4 |
| 2012/0245331 A1* | 9/2012 | Takakura | C07K 14/375 530/402 |

FOREIGN PATENT DOCUMENTS

| | | |
|---|---|---|
| CN | 1203276 | 12/1998 |
| CN | 103525852 | 1/2014 |
| EP | 1924693 | 4/2010 |
| WO | 2007/035323 | 3/2007 |
| WO | WO-2014139130 A1 | 9/2014 |

OTHER PUBLICATIONS

Wei Dissertation 1999 (Year: 1999).*
Glascock & Weichert "Using chromosomal IacIQ1 to control expression of genes on high-copy number plasmids in *Escherichia coli*" (Gene vol. 223, 1998: pp. 221-231). (Year: 1998).*
Blommel et al., "Enhanced Bacterial Protein Expression During Auto-Induction Obtained by Alteration of Lac Repressor Dosage and Medium Composition", Biotechnol Prog., vol. 23, No. 3, pp. 585-598, May 1, 2007.
Nocadello et al. "The new pLAI (lux regulon based auto-inducible) expression system for recombinant protein production in *Escherichia coli*", Microbial Cell Factories, Dec. 31, 2012, 11:3.
Studier, F. William, "Stable expression clones and auto-induction for protein production in *E. coli*", Structural Genomics: General Application, Methods In Molecular Biology, Oct. 12, 2013.
Wagner et al. "Tuning *Escherichia coli* for membrane protein overexpression", PNAS, Sep. 23, 2008, 38 105.
International Search Report for corresponding PCT Application No. PCT/CN2014/094388, dated Sep. 16, 2015.
Vos De W M et al: "Expression of Systems for Industrial Gram-Positive Bacteria with Low Guanine and Cytosine Content". Current Opinion in Biotechnology, London, GB, vol. 8, No. 5, Jan. 1, 1997 (Jan. 1, 1997), pp. 547-553, XP001010644, ISSN: 0958-1669, DOI: 10. 1016/S0958-1669(97)80027-4.
Zhou X X et al: "The nisin-controlled gene expression system: Construction, application and improvements", Biotechnology Advances, Elsevier Publishing, Barking, GB, vol. 24, No. 3, May 1, 2006 (May 1, 2006), pp. 285-295, XP028005962, ISSN: 0734-9750, DOI: 10. 1016/J.BIOTECHADV.2005.11.001 [retrieved on May 1, 2006].
Glascock et al., "Using chromosomal IacIQ1 to control expression of genes on high-copy-number plasmids in *Escherichia coli*," Gene, 1998, vol. 223, pp. 221-231.
Charleygao, "pLysS & pLysE," Baidu Library, Jun. 4, 2010; https://wenku.baidu.com/view/bfe002d4b14e852458fb5737.html.
Barbas et al., (1991). "Assembly of combinatorial antibody libraries on phage surfaces: the gene III site," PNAS USA, 88(18):7978-7982.
Boynton et al., (1999). "Reduction of Cell Lysate Viscosity during Processing of Poly(3-Hydroxyalkanoates) by Chromosomal Integration of the Staphylococcal Nuclease Gene in Pseudomonas putida," Appl. Environ. Microbiol., 65(4):1524-1529.

(Continued)

*Primary Examiner* — Catherine S Hibbert
(74) *Attorney, Agent, or Firm* — Morrison & Foerster LLP

(57) ABSTRACT

Methods and systems for autoinduction of gene expression, without the need to add exogenous inducers. A dual genetic element system, which includes a first, high copy number genetic element comprising a first gene of interest that is under the control of an inducible promoter, and a second, low copy number genetic element comprising a gene encoding a transcriptional factor which, upon expression, regulates transcription from the inducible promoter, wherein activation of transcription from the inducible promoter does not require addition of an exogenous inducer.

14 Claims, 10 Drawing Sheets

Specification includes a Sequence Listing.

(56) References Cited

OTHER PUBLICATIONS

Chen et al., (2013). "Characterization of 582 natural and synthetic terminators and quantification of their design constraints," Nature Methods, 10:659-664.
Cooke et al., (2003). "A modified *Escherichia coli* protein production strain expressing staphylococcal nuclease, capable of autohydrolysing host nucleic acid." J Biotechnol., 101:229-239.
Deuschle et al., (1986). "Promoters of *Escherichia coli*: a hierarchy of in vivo strength indicates alternate structures," EMBO J, 5(11):2987-2994.
Hochberg et al., (2014). "The structured core domain of αB-crystallin can prevent amyloid fibrillation and associated toxicity," PNAS USA, 111:E1562-E1570.
Hoet et al., (2005). "Generation of high-affinity human antibodies by combining donor-derived and synthetic complementarity-determining-region diversity," Nat Biotechnol., 23(3):344-348.
Krebber et al., (1996). "Inclusion of an upstream transcriptional terminator in phage display vectors abolishes background expression of toxic fusions with coat protein g30," Gene, 178:71-74.
Makoff et al., (1991). "High level heterologous expression in *E. coli* using mutant forms of the lac promoter," Nucleic Acids Res, 19(9):2417-2421.
Rosano et al., (2014). "Recombinant protein expression in *Escherichia coli*: advances and challenges," Frontiers in Microbiology, 5:172, 17 pages.
Simmons et al., (2002). "Expression of full-length immunoglobulins in *Escherichia coli* rapid and efficient production of aglycosylated antibodies," Journal of Immunological Methods, 263:133-147.
Steukers et al., (2006). "Rapid kinetic-based screening of human Fab fragments," Journal of Immunological Methods, 310:126-135.
Studier, (2005). "Protein production by auto-induction in high density shaking cultures," Protein Expr Purif, 41(1):207-234, 20 pages.
Su et al., (2007). "Automated high-throughput purification of antibody fragments to facilitate evaluation in functional and kinetic based assays," Journal of Immunological Methods, 322:94-103.
Tashiro et al., (2013). "Prefoldin protects neuronal cells from polyglutamine toxicity by preventing aggregation formation," J. Biol. Chem., 288:19958-19972.

\* cited by examiner

1: SB medium
2: SB medium + IPTG

METHODS AND SYSTEMS FOR AUTOINDUCTION OF PROTEIN EXPRESSION

CROSS REFERENCE TO RELATED APPLICATIONS

This application is a U.S. National Phase application under 35 U.S.C. 371 of International Application No. PCT/CN2014/094388, filed Dec. 19, 2014, the disclosure of which is incorporated herein by reference.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 48628966_1.txt, recorded: Nov. 1, 2018, size: 33,984 bytes).

FIELD

The present disclosure relates in general methods and systems for in vitro gene expression, in particular genetic elements such as plasmids carrying regulatory elements.

BACKGROUND

During antibody screening processes such as phage display, it is routine to screen hundreds, or even thousands, of hits to identify the diverse antibody fragments that bind to multiple epitopes of a given target. A sufficient amount of expressed and purified antibody fragments for each of these hits needs to be produced for further characterization. Typically, the genes encoding corresponding antibody fragments are either subcloned en masse to a different expression vector, or the phage display vector carrying the gene of interest are converted into expression vector. Then the expression vector is transformed into a host cell, typically E. coli, and the transformants are inoculated into small volume of cultures (1-3 ml) for overnight growth. When the cultures are grown to exponential phase, an inducer (most commonly isopropyl-β-D-thiogalactoside (IPTG) for lac promoter) is added to the final concentration of 0.1-1 mM to induce expression of antibody fragments.

When dealing with hundreds, or even thousands, of cell cultures at the same time, a significant difficulty is to ensure all of the cultures are in a substantially similar state of growth before induction. Differences in lag time or growth rate typically generate a situation where different cultures are in different growth phase and will be ready for induction at different times. Usually considerable effort is required to follow growth of different cultures by measuring optical density (OD) at 600 nm (OD600) at various time points, and then add IPTG to each culture at proper time individually.

Therefore there are advantages for an autoinduction expression system that require no monitoring of growth phases of numerous cultures and no addition of inducers after colonies have been inoculated into liquid culture. The first autoinduction system was developed by F. William Studier (Studier (2005) Protein Expr Purif 41(1): 207-234). This system was based on the popular pET bacterial expression system, in which the target protein is controlled by the powerful T7 promoter that is very specifically recognized by T7 RNA polymerase. The T7 RNA polymerase, in turn, is placed under control of the well-characterized inducible lac promoter. It is widely accepted that the wild type lac promoter commonly used in bacterial expression of proteins is too weak to express target proteins directly (Rosano et al (2014) Frontiers in Microbiology 5(172) 1-17; Deuschle et al. (1986) EMBO J 5(11): 2987-2994; Makoff et al. (1991) Nucleic Acids Res 19(9): 2417-2421), and it is therefore more commonly used in conjunction with other inducible systems such as the T7 expression system. However, it is well known in the field that the T7 promoter-mediated protein expression can be too powerful inside bacterial cells. Thus, T7 promoter is generally not optimal for expressing membrane protein or secreted proteins in E. coli (Wagner et al. (2008) Proc Natl Acad Sci USA 105(38): 14371-14376), because too much protein is produced too quickly in the cytoplasm, and they overwhelm the limited capacity of the bacterial secretion system, which results in accumulation and aggregation of proteins, toxicity to the host cell and eventual killing of the host cell.

A modified pET system designed for membrane protein production employs regulated expression of T7 lysozyme, an inhibitor of T7 RNA polymerase, to dial down the activity of T7 RNA polymerase in order to slow down the protein production rate (Wagner et al. (2008) Proc Natl Acad Sci USA 105(38): 14371-14376). However, this system requires careful titration of the concentration of inducer L-rhamnose. Furthermore, the above existing autoinduction systems are not compatible with phage display systems and require subcloning of the gene of interest from the display vector to a new expression vector, which is time consuming and costly.

Genentech also developed a bacterial expression system that is based on PhoA promoter (Simmons et al., Journal of Immunological Methods 263 (2002) 133-147). The target protein is induced when phosphate concentration in medium is depleted. However, the system requires that the E. coli transformants grow in a special C.R.A.P. phosphate-limiting media, which is quite expensive to make.

Thus, there is a need for an improved autoinduction system that is easy to manipulate, eliminates the need for adding an inducer to induce expression thereby saving time and costs associated with induction, provides desirable level of expression of proteins of interest, in particular difficult to express proteins such as membrane proteins and secreted proteins, and enables seamless conversion from display vector to expression vector.

SUMMARY

Disclosed herein is an autoinduction system and related methods for the production of proteins, as well as methods for making the system. This system does not require the addition of an exogenous inducer to induce expression thereby significantly saving time and costs. Furthermore, compared with known autoinduction systems, the vectors used in this system are simplified, easier to manipulate during cloning and subcloning, and suitable for providing desirable level of expression, in particular proteins that are difficult to express such as membrane proteins and secreted proteins. Additionally, the methods and systems of the present disclosure are compatible with antibody screening systems such as phage display, as they enable seamless conversion from display vector to expression vector, and can be used to successfully express antibody fragments such as Fabs which are secreted into cell periplasm.

One aspect of the present disclosure relates to a system for expression of a gene of interest. The system includes: a first, high copy number genetic element comprising a gene of interest that is under the control of an inducible promoter; and a second, low copy number genetic element comprising a repressor gene encoding a repressor which, upon expression, represses transcription from the inducible promoter; wherein activation of transcription from the inducible promoter does not require addition of an exogenous inducer.

In some embodiments, the first genetic element is a high copy number plasmid, which can optionally be selected from pUC, pBluescript, and pGEM. These plasmids can optionally further comprise a phage origin of replication.

In certain embodiments, the gene of interest encodes a membrane protein or secreted protein, or an antibody fragment.

The inducible promoter in the first genetic element in some instances, can comprise a promoter, an operator and optionally a catabolite activator protein (CAP) binding site. In some embodiments, the inducible promoter can be selected from lac, T7lac, tac, TRE, araBAD, rhaBAD, and/or trp.

In certain embodiments, the first genetic element can further comprise at least one transcriptional terminator.

The second genetic element can be selected from a low copy number plasmid, transposon, host chromosome, artificial chromosome, and/or episome. The low copy number plasmid can be selected from pLysS, pR6K, pACYC, pSC101 and pWSK.

In some embodiments, the transcriptional factor can be a repressor, such as LacI (for repressing lac, T7lac, and/or tac promoter), TetR (for repressing TRE promoter), and/or TrpR (for repressing trp promoter). The transcriptional factor can also be an activator, such as AraC (for activating araBAD promoter), and/or RhaS (for activating rhaBAD promoter).

In certain embodiments, the second genetic element may further comprise one or more of: a nuclease gene, a lysozyme gene, a chaperone gene and a biotin ligase gene.

The first and second genetic element can be present in a host cell. The host cell can be a bacterial cell, a yeast cell, or a mammalian cell. In some embodiments, after culturing in a culture medium a host cell containing the first and second genetic elements for a sufficient period of time such that glucose is depleted, expression of the first gene can be autoinduced by an agent endogenous in the culture medium.

The agent endogenous in the culture medium can be selected from lactose (for activating lac, T7lac, and/or tac promoter), arabinose (for activating araBAD promoter), rhamnose (for activating rhaBAD promoter), tetracycline or a derivative thereof (e.g., doxycycline, minocycline, metacycline, sancycline, chloro-tetracycline, demeclocycline, and tigecycline) (for activating TRE promoter), and/or tryptophan (for activating trp promoter). In some embodiments, the agent is present in the culture medium by a trace or minute amount that is insufficient to induce expression when glucose is present, and only activates expression when the glucose is depleted.

In some embodiments, the sufficient period of time for culturing to achieve autoinduction is about 4 hours or more, about 5 hours or more, about 6 hours or more, about 7 hours or more, about 8 hours or more, about 9 hours or more, about 10 hours or more, about 11 hours or more, about 12 hours or more, about 13 hours or more, about 14 hours or more, about 15 hours or more, or about 20 hours or more.

Also provided herein is a method for expressing a gene of interest, comprising culturing in a culture medium a host cell (e.g., a bacterial cell, a yeast cell, or a mammalian cell) comprising the system disclosed herein, for a sufficient period of time (e.g., about 4 hours or more) such that the gene of interest is expressed. The method can further include autoinducing expression of the gene of interest by an agent endogenous in the culture medium. The agent can be selected from lactose for activating lac, T7lac, and/or tac promoter, arabinose for activating araBAD promoter, rhamnose for activating rhaBAD promoter, tetracycline or a derivative thereof (e.g., doxycycline) for activating TRE promoter, and/or tryptophan for activating trp promoter. The agent may be present in the culture medium by a trace amount that is insufficient to induce expression when glucose is present, and only activates expression when the glucose is depleted. In some embodiments, the method further includes expressing a nuclease for digesting chromosomal DNA of the host cell, and/or a lysozyme for digesting cell wall of the host cell.

Genetic elements for use in the autoinduction system and method are also provided herein. Exemplary genetic elements include plasmids, transposons, host chromosomes, artificial chromosomes, and/or episomes. In one example, a plasmid is provided which comprises p15A origin of replication, chloramphenicol acetyltransferase gene (CAT/CamR), T7 lysozome gene and a multiple cloning site having the sequence of SEQ ID NO. 5, wherein the plasmid does not contain the entire open reading frame of tetracycline efflux protein (TetR) gene. The plasmid can have the sequence of SEQ ID NO. 6. Other exemplary plasmids include SEQ ID NOS. 1, 7, 8 and 9.

Another aspect relates to a method for making the above system. The method includes introducing to a host cell a first, high copy number genetic element comprising a gene of interest that is under the control of an inducible promoter; and introducing to the host cell a second, low copy number genetic element comprising a repressor gene encoding a repressor which, upon expression, represses transcription from the inducible promoter; wherein activation of transcription from the inducible promoter does not require addition of an exogenous inducer.

Further embodiments are illustrated by the following non-limiting drawings, description and examples.

DETAILED DESCRIPTION

Figure 1:
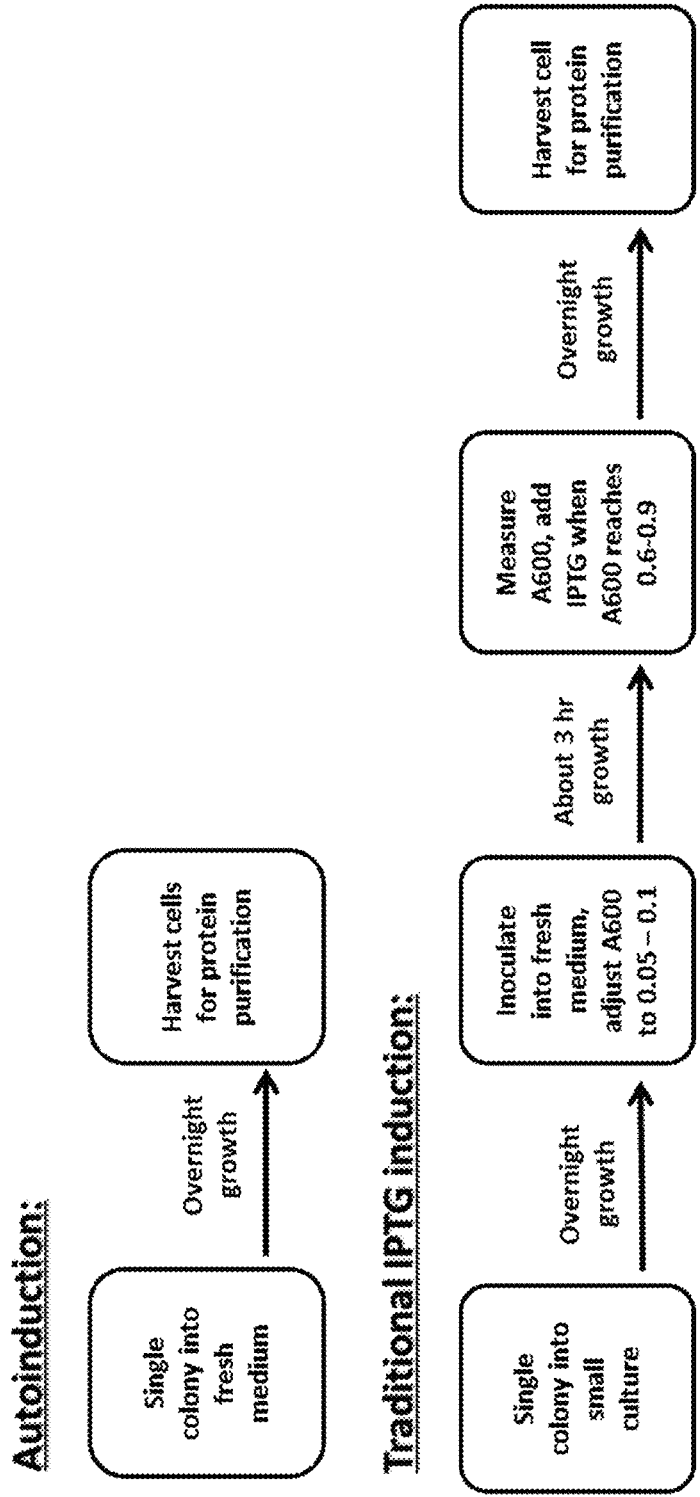
FIG. 1 shows a comparison of the method of the present disclosure and traditional induction of expression.

Systems and methods for autoinduction of protein expression, in some embodiments, include at least two genetic components: 1) a catabolic repression system (e.g., via catabolite activator protein binding site that is operably linked with a gene of interest) so that in the presence of glucose, the basal expression level of the gene of interest is very low; and 2) an operator sequence operably linked with the gene of interest wherein the operator is occupied by repressors or lacking activators in the absence of inducers, so as to prevent transcription by RNA polymerase. In addition, a minute amount of inducer is present in the culture medium (e.g., as an intrinsic component of the culture medium or being premixed with the culture medium). Such minute amount is insufficient to induce transcription in the presence of glucose, due to catabolic repression. When glucose is depleted, catabolic repression is removed such that the minute amount of inducer can bind the repressor to derepress transcription, or bind the activator to activate transcription. Exemplary operator-repressor pair include lac-LacI, Tet-TetR and Trp-TrpR, where the repressor genes and the target genes under the control of their cognate operator can be placed in separate genetic elements. Positively regulated expression systems, such as the pBAD system (using AraC as activator and arabinose as inducer) or L-rhamnose inducing system (using RhaS as activator and L-rhamnose as inducer), can also be used herein. For example, the activator can be in the low copy number genetic element under catabolic repression, so that the activator will not be expressed until glucose is depleted.

It has been surprisingly found that using the system of the present disclosure, autoinduction can be successfully achieved without the need to add exogenous inducers. The result is surprising for several reasons. First, conventionally repressor genes are cloned into the same high copy number plasmid carrying the target gene, to ensure sufficient amount of repressor is expressed to repress expression of the target gene. Initial repression, before activation of expression, is important because unwanted expression of an exogenous protein, in particular membrane proteins and secreted proteins, during growth state of the host cells can create stress and even toxicity to the cellular machinery of the host cell, as expression of exogenous proteins competes with the host cell for various machineries for transcription, translation, protein folding, and protein translocation, as well as other resources. Here, it is surprisingly found that a repressor gene carried by a low copy number genetic element is sufficient to repress expression of a target gene carried by a high copy number genetic element. Second, repression can be reversed after a relatively short period of time of culturing (e.g., about 4 hours) to allow sufficient expression of the target gene. Third, reversion of the repression does not require exogenous inducer. While not wishing to be bound by theory, it is believed that in the case of lac promoter (or its modifications or derivatives such as T7lac and tac), a trace amount of lactose (e.g., less than 0.1 mM, less than 0.01 mM or less than 0.001 mM) is present in the culture medium (e.g., from yeast extract) which is capable to bind and remove the lacI repressor once glucose present in the culture medium is depleted (after culturing for a period of time). In contrast, when there is significant amount of glucose remaining in the culture medium, glucose represses lac promoter, or prevents lactose from being imported into the cell. For other inducible promoters, a trace amount of corresponding inducer (e.g., less than 0.1 mM, less than 0.01 mM or less than 0.001 mM) may be pre-mixed in the culture medium before culturing.

Compared with conventional methods, the method and system of the present disclosure significantly saves time and cost associated with induction. As shown in FIG. 1, compared to the traditional IPTG induction which typically requires constant monitoring of growth state of bacterial culture and two overnight growth (Su et al. (2007) Journal of Immunological Methods 322: 94-103; Steukers et al. (2006) Journal of Immunological Methods 310: 126-135), the autoinduction system of the present disclosure only requires one overnight growth, eliminates the need of monitoring growth state, and saves a substantial amount of time and cost. The time and cost saving is particularly significant when large number of samples (e.g., hundreds or thousands during antibody screening) are involved.

Another advantage of the system of the present disclosure is its compatibility with phage display. For example, the high copy number plasmid carrying the target gene can be designed to be used first as a display vector, which can be converted to an expression vector. This can be done by including two origins of replication on the plasmid, one being a phage origin of replication (e.g., f1), the other a bacterial origin of replication. Such a convertible plasmid is disclosed in PCT International Publication No. WO 2014/139130 by Adagene Inc., which is incorporated herein by reference in its entirety.

In some embodiments, the system is a dual plasmid system. In one example, the first plasmid is DPA1 (dual plasmid autoinduction 1) which is based on the multicopy pBluscript KS(+) backbone, and the inducible promoter used for expression of proteins, including for example Fabs and membrane proteins, is a lac promoter which can be wild-type or modified. In one example, the lac promoter is a modified version that is devoid of any sequence of the lacI ORF, in contrast to the lac promoters that are used by others (Hoet et al. (2005) Nat Biotechnol 23(3): 344-348; Barbas et al. (1991) Proc Natl Acad Sci USA 88(18): 7978-7982; Krebber et al. (1996) Gene 178: 71-74) that contain C-terminal fragment of lacI. Because lac promoter is known to be leaky (i.e., transcription takes place even in the absence of an inducer and/or in the presence of a repressor), and such leaky expression can stress the host cell and affect its growth, two measures are taken to reduce basal expression of target proteins: 1) a strong bacterial transcriptional terminator is placed upstream of the lac promoter; and 2) the $lacI^q$ gene encoding lac repressor is cloned into a separate low-copy number plasmid DPA2 that is compatible with DPA1. As shown herein, this dual plasmid system tightly suppresses basal expression of target proteins, while at the same time, allowing autoinduction of target proteins without adding inducers such as IPTG.

It is to be understood that both the foregoing general description and the following detailed description are exemplary and explanatory only and are not restrictive of the compositions and methods described herein. In this application, the use of the singular includes the plural unless specifically stated otherwise. Also, the use of "or" means "and/or" unless state otherwise. Similarly, "comprise," "comprises," "comprising," "include," "includes" and "including" are not intended to be limiting. It is understood that aspects and embodiments of the disclosure described herein include "consisting" and/or "consisting essentially of" aspects and embodiments.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

As used herein, the following terms and phrases are intended to have the following meanings:

The articles "a" and "an" are used herein to refer to one or to more than one (i.e., to at least one) of the grammatical object of the article. By way of example, "an element" means one element or more than one element.

By "a population of hosts" is meant a group of hosts into which a library of polynucleotides can be introduced and displayed. The host can be phages, yeasts, bacteria or mammalian cells. In some embodiments, a population of cells from a monoculture, i.e., wherein each cell in the population is of the same cell type can be used. Alternatively, mixed cultures of cells can also be used. Cells may be adherent, i.e., cells which grow attached to a solid substrate, or, alternatively, the cells may be in suspension. Mammalian cells may be cells derived from primary tumors, cells derived from metastatic tumors, primary cells, cells which have lost contact inhibition, transformed primary cells, immortalized primary cells, cells which may undergo apoptosis, and cell lines derived there from.

As used herein, the term "about" means within 20%, more preferably within 10% and most preferably within 5%. The term "substantially" means more than 50%, preferably more than 80%, and most preferably more than 90% or 95%.

As used herein, the term "amino acid sequence" refers to a sequence of contiguous amino acid residues of any length. The terms "polypeptide," "peptide," "oligopeptide," or "protein" may be used interchangeably herein with the term "amino acid sequence."

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single antibody; (vi) the dAb fragment which consists of a VH domain; (vii) isolated CDR regions; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd segments (VH-CH1-VH-CH1) which, together with complementary light chain polypeptides, form a pair of antigen binding regions.

Catabolite activator protein (also known as cyclic AMP receptor protein, "CAP") binding site is a DNA sequence to which CAP, once activated by cyclic adenosine monophosphate (cAMP), binds and assists the RNA polymerase in binding to the DNA. cAMP is a signal molecule whose prevalence is inversely proportional to that of glucose. As a result, in the absence of glucose, the cAMP concentration is high and binding of CAP-cAMP to the DNA significantly increases transcription. CAP binding site sequence is well known in the art.

"Copy number" of a genetic element, plasmid or vector refers to how many copies are present in a host cell. Copy number is generally determined by the origin of replication ("ORI") used and can be manipulated with mutations in the ORI. For example, the pMB1 ORI maintains about 20 copies per cell, while pUC—which contains a derivative of the pMB1 ORI differs by only two mutations—will produce as many as 700 copies per cell. A "high copy number" genetic element or plasmid is one that is capable of replicating itself till at least, for example, 100 copies are present per cell. Commonly used high copy number plasmids include pUC (pMB1 derivative ORI), pBluescript (ColE1 derivative ORI), and pGEM (pMB1 derivative ORI). A "low copy number" genetic element or plasmid is present at, e.g., less than about 20 copies per cell. Commonly used low copy number plasmids include pBR322 (pMB1 ORI), pET (pMB1 ORI), pGEX (pMB1 ORI), pColE1 (ColE1 ORI), pR6K (R6K ORI), pACYC (p15A ORI), pSC101 (pSC101 ORI) and pLys (p15A ORI). The low copy number genetic element may be a chromosome of the host cell where endogenous gene(s) are present and/or heterologous genes and/or other sequences are integrated therein. For example, the host can have one or more endogenous genes that encode a transcriptional factor useful for regulating expression of a gene of interest from another genetic element. One or more copies of foreign gene(s) can also be introduced into the host genome via, for example, transposons or recombination. In some embodiments, the autoinduction system of the present disclosure includes a first, high copy genetic element and a second, low copy genetic element. In instances where two plasmids are used, they should be compatible with each other when introduced into the same host. Generally speaking, plasmids with the same ORIs are incompatible because they will compete for the same machinery, creating an unstable and unpredictable environment. As a rule, plasmids from the same group should not be co-transformed. Commonly used plasmids pUC, pBR322, pET, pGEX, pColE1, pBluescript, and pGEM, in some embodiments are in one group. Plasmids pR6K, pACYC, pSC101, pWSK and pLys may be in a different group. In another embodiment, pACYC and pLys both having p15A ORI can be in the same group. pR6K having R6K ORI and pSC101 and pWSK both having pSC101 ORI can belong to different incompatibility groups.

As used herein, the term "display vector" refers to a plasmid or phage DNA or other DNA sequence which is able to replicate autonomously in a host, and capable of expressing and displaying an insert in the vector as part of a fusion protein on the surface of the host.

The term "expression vector" refers to a vector capable of expressing of a gene or any open reading frame that has been cloned into it. Such expression can occur after transformation into a host cell, or in in vitro systems. The cloned DNA or insert is usually operably linked to one or more regulatory sequences, such as promoters, activator/repressor binding sites, terminators, enhancers and the like.

A "genetic element" may be any coding or non-coding nucleic acid sequence that is capable of self replicating. Genetic elements may include one or more origins for replication, operons, genes, gene fragments, exons, introns, markers, regulatory sequences, promoters, operators, catabolite activator protein (also known as cyclic AMP receptor protein, "CAP") binding sites, enhancers, transcriptional terminators, or any combination thereof, which can be operably linked together. Examples include plasmid, phage vector, phagemid, transposon, cosmid, chromosome, artificial chromosome, episome, virus, virion, etc. In some instances, "genetic element" and "vector" are used interchangeably.

A "host" is intended to include any individual virus or cell or culture thereof that can be or has been a recipient for vectors or for the incorporation of exogenous nucleic acid molecules, polynucleotides, and/or proteins. It also is intended to include progeny of a single virus or cell. The progeny may not necessarily be completely identical (in morphology or in genomic or total DNA complement) to the original parent cell due to natural, accidental, or deliberate mutation. The virus can be phage. The cells may be prokaryotic or eukaryotic, and include but are not limited to bacterial cells, yeast cells, insect cells, animal cells, and mammalian cells, e.g., murine, rat, simian, or human cells.

An "insert" as used herein, is a heterologous nucleic acid sequence that is ligated into a compatible site into a vector. An insert may comprise one or more nucleic acid sequences that encode a polypeptide or polypeptides. An insert may comprise regulatory regions or other nucleic acid elements.

An "isolated" or "purified" polypeptide or polynucleotide, e.g., an "isolated polypeptide," or an "isolated polynucleotide" is purified to a state beyond that in which it exists in nature. For example, the "isolated" or "purified" polypeptide or polynucleotide, can be substantially free of (e.g., having less than about 50%, 40%, 30%, 20%, 10% or 5% (by dry weight) of) cellular material or other contaminating proteins from the cell or tissue source from which the protein or polynucleotide is derived, or substantially free from chemical precursors or other chemicals when chemically synthesized.

The terms "marker" or "reporter" refer to a gene or protein that can be attached to a regulatory sequence of another gene or protein of interest, so that upon expression in a host cell or organism, the reporter can confer certain characteristics that can be relatively easily selected, identified and/or measured. Reporter genes are often used as an indication of whether a certain gene has been introduced into or expressed in the host cell or organism. Examples of commonly used reporters include: antibiotic resistance genes, auxotropic markers, β-galactosidase (encoded by the bacterial gene lacZ), luciferase (from lightning bugs), chloramphenicol acetyltransferase (CAT; from bacteria), GUS (β-glucuronidase; commonly used in plants) and green fluorescent protein (GFP; from jelly fish). Reporters or markers can be selectable or screenable. A selectable marker (e.g., antibiotic resistance gene, auxotropic marker) is a gene confers a trait suitable for artificial selection; typically host cells expressing the selectable marker is protected from a selective agent that is toxic or inhibitory to cell growth. A screenable marker (e.g., gfp, lacZ) generally allows researchers to distinguish between wanted cells (expressing the marker) and unwanted cells (not expressing the marker or expressing at insufficient level).

"Nucleic acid," "nucleic acid sequence," "oligonucleotide," "polynucleotide," "gene" or other grammatical equivalents as used herein means at least two nucleotides, either deoxyribonucleotides or ribonucleotides, or analogs thereof, covalently linked together. Polynucleotides are polymers of any length, including, e.g., 20, 50, 100, 200, 300, 500, 1000, 2000, 3000, 5000, 7000, 10,000, etc.

"Operator" is a DNA sequence to which a transcription factor binds to regulate gene expression. The transcription factor is typically a repressor, which can bind to the operator to prevent transcription. For example, in the lac system, the operator can be bound by the lac repressor (encoded by lacI gene) in the absence of lactose to prevent transcription. When lactose is present (and glucose level is low), a lactose metabolite called allolactose (a combination of glucose and galactose) binds to the lac repressor, causing a change in its shape. The resulting altered repressor is unable to bind to the operator, allowing RNA polymerase to transcribe the downstream genes.

The terms "peptide," "polypeptide" and "protein" used herein refer to polymers of amino acid residues. These terms also apply to amino acid polymers in which one or more amino acid residues is an artificial chemical mimetic of a corresponding naturally occurring amino acid, as well as to naturally occurring amino acid polymers, those containing modified residues, and non-naturally occurring amino acid polymers. In the present case, the term "polypeptide" encompasses an antibody or a fragment thereof.

"Plasmid" is a small circular piece of DNA that replicates independently from the host's chromosomal DNA. The host can be bacteria, yeast, plant, or mammalian cells. Plasmids typically have an origin of replication, a selection marker, and one or more cloning sites. A plasmid can contain two or more different origins of replication, such that it can shuttle between two or more different hosts.

As used herein, the term "promoter" refers to a DNA sequence capable of controlling the transcription of a nucleotide sequence of interest into mRNA, and generally contains a RNA polymerase binding site and one or more operators and/or catabolite activator protein (also known as cyclic AMP receptor protein, "CAP") binding sites for biding of other transcriptional factors. A promoter may be constitutively active ("constitutive promoter") or be controlled by other factors such as a chemical, heat or light. The activity of an "inducible promoter" is induced by the presence or absence or biotic or abiotic factors. Aspects of the disclosure relate to an "autoinducible" or "autoinduction" system where an inducible promoter is used, but addition of exogenous inducer is not required. Commonly used constitutive promoters include CMV, EF1a, SV40, PGK1, Ubc, human beta actin, CAG, Ac5, Polyhedrin, TEF1, GDS, ADH1 (repressed by ethanol), CaMV35S, Ubi, H1, U6, T7 (requires T7 RNA polymerase), and SP6 (requires SP6 RNA polymerase). Common inducible promoters include TRE (inducible by Tetracycline or its derivatives; repressible by TetR repressor), GAL1 & GAL10 (inducible with galactose; repressible with glucose), lac (constitutive in the absence of lac repressor (LacI); can be induced by IPTG or lactose), T7lac (hybrid of T7 and lac; requires T7 RNA polymerase which is also controlled by lac operator; can be induced by IPTG or lactose), araBAD (inducible by arabinose which binds repressor AraC to switch it to activate transcription; repressed catabolite repression in the presence of glucose via the CAP binding site or by competitive binding of the anti-inducer fucose), trp (repressible by tryptophan upon binding with TrpR repressor), tac (hybrid of lac and trp; regulated like the lac promoter; e.g., tacI and tacII), and pL (temperature regulated). The promoter can be prokaryotic or eukaryotic promoter, depending on the host. Common promoters and their sequences are well known in the art.

As used herein, unless otherwise stated, the term "transcription" refers to the synthesis of RNA from a DNA template; the term "translation" refers to the synthesis of a polypeptide from an mRNA template. Transcription and translation collectively are known as "expression."

The term "transfected" or "transformed" or "transduced" as used herein refers to a process by which exogenous nucleic acid is transferred or introduced into the host cell. A transformed cell includes the primary subject cell and its progeny. The host cell can be bacteria, yeasts, mammalian cells, and plant cells.

As used herein, the term "vector" refers to a nucleic acid molecule capable of transporting another nucleic acid to which it has been linked. A vector includes any genetic element, such as a plasmid, phage vector, phagemid, transposon, cosmid, chromosome, artificial chromosome, episome, virus, virion, etc., capable of replication (e.g., containing an origin of replication which is DNA sequence allowing initiation of replication by recruiting replication machinery proteins) when associated with the proper control elements and which can transfer gene sequences into or between hosts. One type of vector is an episome, i.e., a nucleic acid capable of extra-chromosomal replication. Another type of vector is an integrative vector that is designed to recombine with the genetic material of a host cell. Vectors may be both autonomously replicating and integrative, and the properties of a vector may differ depending on the cellular context (i.e., a vector may be autonomously replicating in one host cell type and purely integrative in another host cell type). Vectors generally contain one or a small number of restriction endonuclease recognition sites and/or sites for site-specific recombination. A foreign DNA fragment may be cleaved and ligated into the vector at these sites. The vector may contain a marker suitable for use in the identification of transformed or transfected cells. For example, markers may provide antibiotic resistant, fluorescent, enzymatic, as well as other traits. As a second example, markers may complement auxotrophic deficiencies or supply critical nutrients not in the culture media.

Other terms used in the fields of recombinant nucleic acid technology, microbiology, immunology, antibody engineering, and molecular and cell biology as used herein will be generally understood by one of ordinary skill in the applicable arts.

Dual Genetic Element Autoinduction

The autoinduction system can be used to express a variety of proteins, in particular membrane proteins, secreted proteins, antibodies and antibody fragments. In some embodiments, the autoinduction system of the present disclosure includes two genetic elements. Exemplary genetic elements include plasmids, transposons, host chromosomes, artificial chromosomes, and/or episomes. The system can include: a first, high copy number genetic element comprising a gene of interest that is under the control of an inducible promoter; and a second, low copy number genetic element comprising a repressor gene encoding a repressor which, upon expression, represses transcription from the inducible promoter; wherein activation of transcription from the inducible promoter does not require addition of an exogenous inducer.

In some embodiments, the first genetic element is a high copy number plasmid, which can optionally be selected from pUC, pBluescript, and pGEM. These plasmids can optionally further comprise a phage origin of replication such that they can shuffle between different hosts, e.g., phage and bacterium. This facilitates conversion from phage display vector to expression vector, using methods described in, for example, PCT International Publication No. WO 2014/139130 by Adagene Inc., which is incorporated herein by reference in its entirety. The second genetic element can be selected from a low copy number plasmid, transposon, host chromosome, artificial chromosome, and/or episome. The low copy number plasmid can be selected from pLysS, pR6K, pACYC, pSC101 and pWSK. When two plasmids are used, they should be compatible with each other when introduced into the same host. Generally speaking, plasmids with the same ORIs are incompatible because they will compete for the same machinery, creating an unstable and unpredictable environment. As a rule, plasmids from the same group should not be co-transformed. Plasmids pUC, pBR322, pET, pGEX, pColE1, pBluescript, and pGEM, in some embodiments are in one group. Plasmids pR6K, pACYC, pSC101, pWSK and pLys may be in a different group. In another embodiment, pACYC and pLys both having p15A ORI can be in the same group. pR6K having R6K ORI and pSC101 and pWSK both having pSC101 ORI can belong to different incompatibility groups.

The inducible promoter in the first genetic element in some instances, can comprise a promoter, an operator and optionally a catabolite activator protein (CAP) binding site. The promoter can provide a binding site for RNA polymerase to initiate transcription. The operator can be bound by other transcriptional factors to repress or activate transcription. The CAP binding site can be bound by CAP-cAMP to enhance transcription, where cAMP level is inversely proportional to glucose level in the culture medium. That is, when glucose level is low, cAMP level is high and transcription level is increased due to enhanced binding of cAMP with CAP and in turn, with CAP binding site. This CAP binding site, CAP and cAMP system, by way of its response to glucose level, can act as a catabolic repression system.

In some embodiments, the inducible promoter can be selected from lac, T7lac, tac, TRE, araBAD, rhaBAD, and/or trp. Correspondingly, depending on the inducible promoter, the transcriptional factor expressed from second genetic element can be a repressor or activator. In some embodiments, the transcriptional factor can be a repressor, such as LacI (for repressing lac, T7lac, and/or tac promoter), TetR (for repressing TRE promoter), and/or TrpR (for repressing trp promoter). The transcriptional factor can also be an activator, such as AraC (for activating araBAD promoter), and/or RhaS (for activating rhaBAD promoter) The gene encoding the transcriptional factor can be placed under the control of a constitutive promoter (e.g., in the case of a repressor), or an inducible promoter (e.g., in the case of an activator). For example, the activator gene can be placed under the control of one or more CAP binding sites such that it is not expressed until glucose is depleted.

In certain embodiments, the first genetic element can further comprise at least one transcriptional terminator. Any known terminators, in particular strong terminators can be used, such as those described in Chen et al. (2013) Nature Methods 10: 659-664, which is incorporated herein by reference in its entirety. In some examples, the transcriptional terminator can be tHP terminator (e.g., SEQ ID NO. 2) or lamda terminator (e.g., SEQ ID NO. 4). The transcriptional terminator may be placed upstream or downstream to the inducible promoter.

In certain embodiments, the second genetic element may further comprise one or more of: a nuclease gene, a lysozyme gene, a chaperone gene and a biotin ligase gene. Each may be present in single copy or multiple copies. Nuclease can help digest host DNA and/or RNA. Lysozyme can damage and degrade cell wall. Chaperone can assist protein folding and maturation. For example, certain chaperones such as prefoldin (Tashiro et al., J. Biol. Chem. 2013, 288:19958-19972) and the core domain of αB-crystallin (Hochberg et al. (2014) Proc Natl Acad Sci USA: E1562-E1570) can prevent protein aggregation; protein disulfide isomerase PDI and proline isomerase can catalyze protein folding. Biotin ligase (e.g., BirA) can be included so that protein with one or more avidin, streptavidin and/or Neutravidin tag that is expressed from DPA1 plasmid can be biotinylated in vivo in a site-specific fashion, to facilitate future purification and identification. Thus, including one or more of nucleases, lysozymes, chaperones and/or biotin ligase in the system facilitates isolation, purification, folding and/or modification of the expressed protein of interest. In one example, the second genetic element comprises both a nuclease gene and a lysozyme gene.

The first and second genetic elements can be present in a host cell. The host cell can be a bacterial cell, a yeast cell, or a mammalian cell. In some embodiments, the first genetic element is a plasmid while the second genetic element is a host chromosome or episome. The plasmid can contain a target gene to be expressed, under the control of an inducible promoter, and can be transformed into the host cell. The host chromosome or episome can contain one or more copies of a gene (and optionally regulatory sequences) encoding a corresponding transcriptional factor, which may be an endogenous gene previously present in the host genome, and/or a heterologous gene integrated into the host chromosome or episome. It has been observed that in some host strains such as bacteria TG1 harboring F' factor (an episome) that has a $lacI^q$ allele, autoinduction works.

The above system can be used to express any gene of interest, by culturing in a culture medium a host cell (e.g., a bacterial cell, a yeast cell, or a mammalian cell) comprising the system for a sufficient period of time such that the gene of interest is expressed. Expression is autoinduced by an agent endogenous in the culture medium. The agent can be selected from lactose (for activating lac, T7lac, and/or tac promoter), arabinose (for activating araBAD promoter), rhamnose (for activating rhaBAD promoter), tetracycline or a derivative thereof (e.g., doxycycline, minocycline, metacycline, sancycline, chloro-tetracycline, demeclocycline, and tigecycline) (for activating TRE promoter), and/or tryptophan (for activating trp promoter). In some embodiments, the agent is present in the culture medium by a trace or minute amount that is insufficient to induce expression when glucose is present, and only activates expression when the glucose is depleted.

In some embodiments, the sufficient period of time for culturing to achieve autoinduction is about 4 hours or more, about 5 hours or more, about 6 hours or more, about 7 hours or more, about 8 hours or more, about 9 hours or more, about 10 hours or more, about 11 hours or more, about 12 hours or more, about 13 hours or more, about 14 hours or more, about 15 hours or more, or about 20 hours or more.

After culturing, the expressed protein can be isolated and purified from the culture such that it is substantially free of (e.g., having less than about 50%, 40%, 30%, 20%, 10% or 5% (by dry weight) of) cellular material or other contaminating proteins from the host cell. In some embodiments, a nuclease for digesting chromosomal DNA of the host cell, and/or a lysozyme for digesting cell wall of the host cell can be coexpressed to facilitate protein isolation and purification.

EXAMPLES

Construction, design and use of exemplary genetic elements are illustrated by the following non-limiting examples. Various sequences used hereunder are summarized in Table 1 below.

TABLE 1

| SEQ ID NO. | Sequence information |
|---|---|
| 1 | DPA1 plasmid sequence |
| 2 | tHP sequence |
| 3 | pLac sequence |
| 4 | lamda terminator sequence |
| 5 | Multiple cloning site of pLysS MCS plasmid |
| 6 | pLysS MCS plasmid sequence |
| 7 | DPA2 plasmid sequence |
| 8 | DPA2-nucA plasmid sequence |
| 9 | DPA2-nucB plasmid sequence |

Example 1

The Construction of Plasmid DPA1

The first plasmid DPA1 (dual plasmid autoinduction 1) is based on the multicopy pBluscript KS(+) backbone, and the promoter used for expression of proteins is a lac promoter (SEQ ID NO. 3) that is devoid of any sequence of lacI ORF. This shorter lac promoter is fully functional in that it can be fully repressed by lacI repressor, and can be induced by inducers such as lactose or IPTG. Target genes can be cloned into multiple cloning sites downstream of the lac promoter (here NdeI and XbaI sites are used as examples). To reduce basal or leaky expression, the lac promoter is preceded by a strong tHP transcriptional terminator (SEQ ID NO. 2). In addition, a lamda terminator (SEQ ID NO. 4), another strong transcriptional terminator, is placed downstream of the target gene to further reduce leaky expression.

Figure 2:
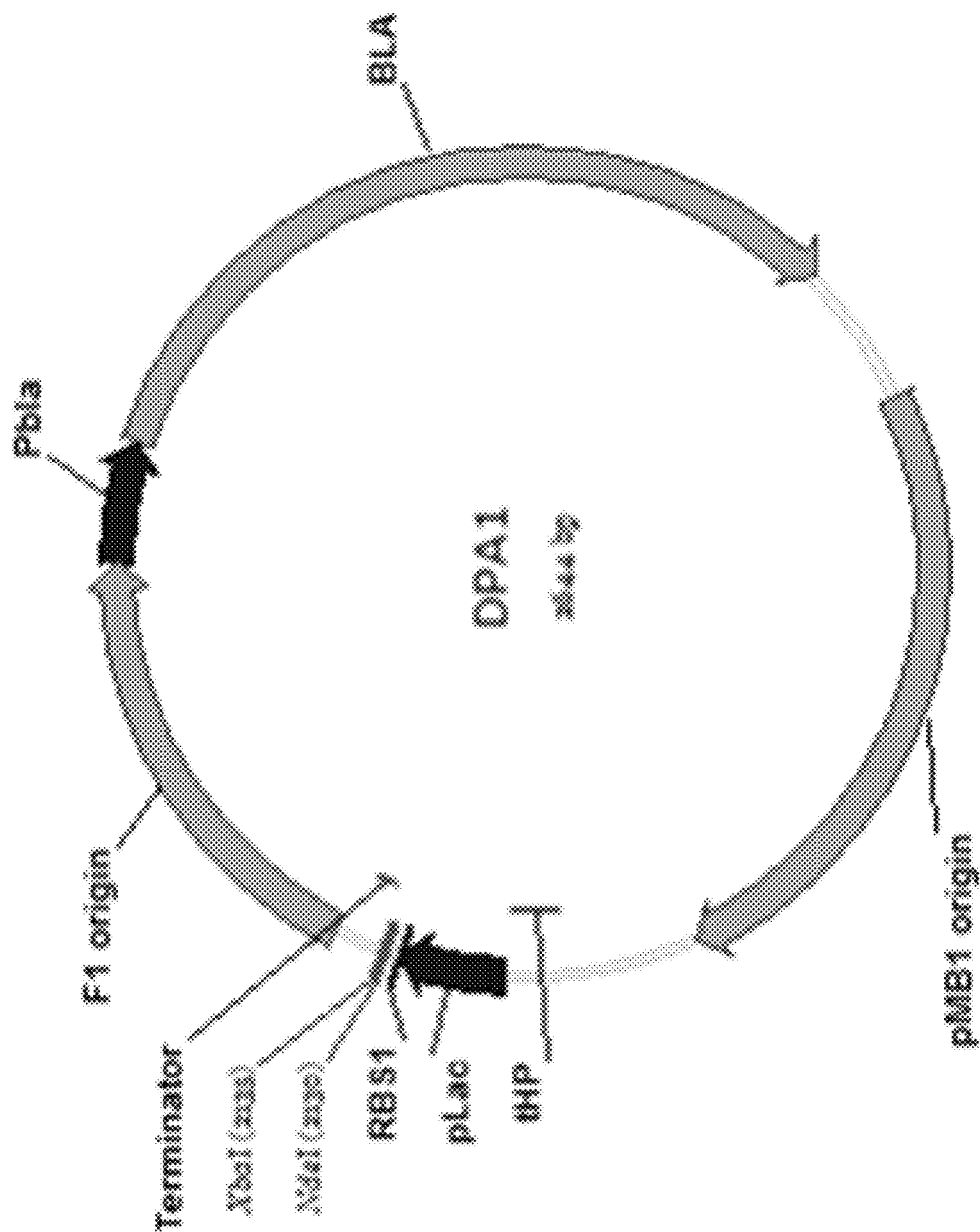
FIGS. 2, 3A and 3B each provide a schematic map showing an exemplary plasmid of the present disclosure.

DPA1 plasmid map is shown in FIG. 2. The entire sequence is shown in SEQ ID NO. 1.

The size of plasmid DPA1 is kept to minimal in order to 1) allow easy propagation and manipulation of plasmid, 2) allow insertion of large foreign genes, including genes encoding membrane proteins, and 3) allow phage packaging when used as display vector.

To further reduce basal expression of target proteins, the $lacI^q$ gene (an allele with a promoter mutation that increases the intracellular concentration of LacI repressor) encoding LacI repressor is cloned into a separate low-copy plasmid DPA2 that is compatible with DPA1. This is in direct contrast to previous approaches (Gene 1995, NAR 1993), where $lacI^q$ gene was cloned into the same high-copy vector. We discovered that LacI repressor expressed from the $lacI^q$ gene present in low-copy plasmid is sufficient to suppress basal expression, while at the same time, allow autoinduction of target proteins.

Example 2

The Construction of the Plasmid pLysS MCS

Figure 3A:
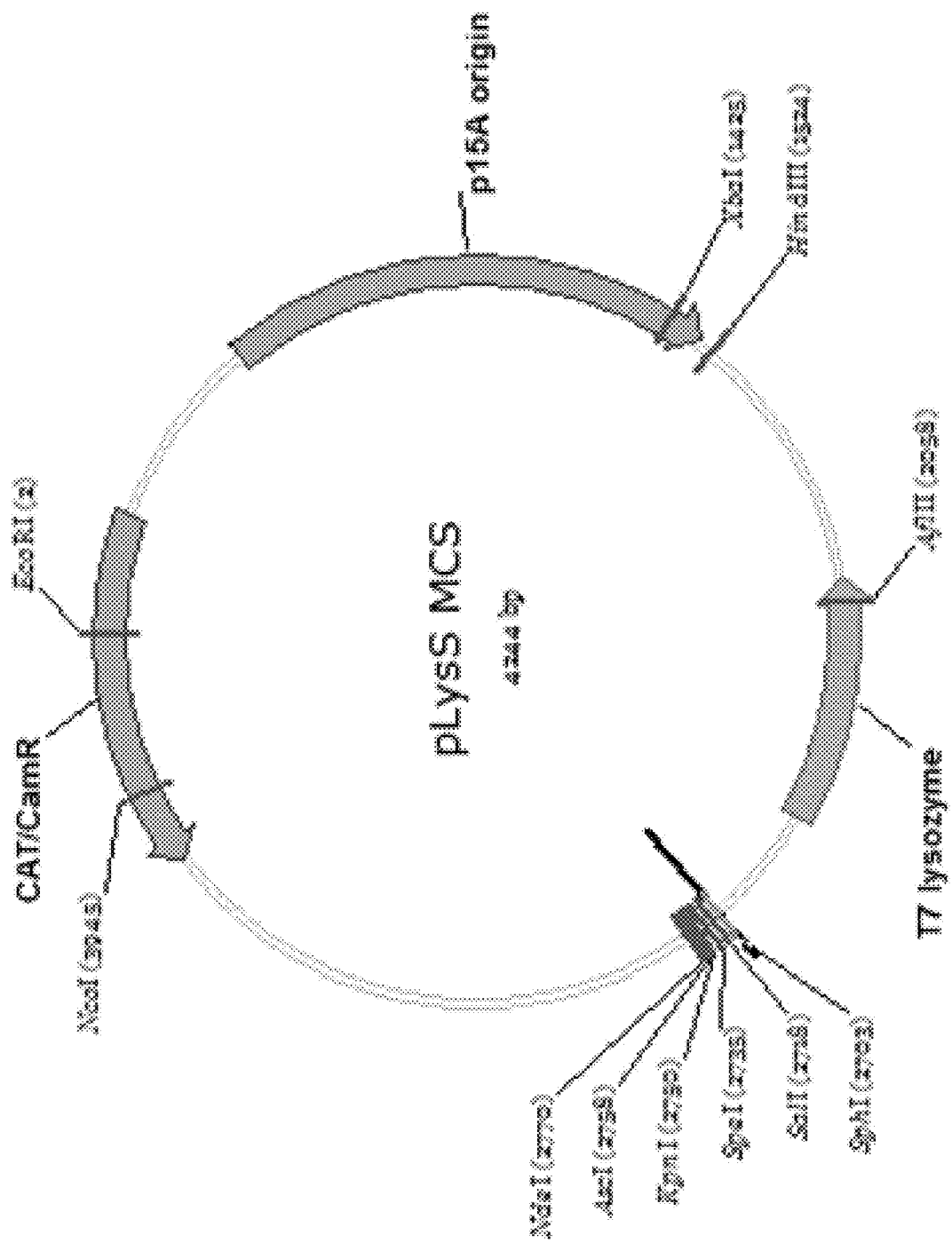

The plasmid pLysS MCS was constructed to allow insertion of multiple DNA fragments into the vector pLysS. We chose the Tet ORF in the vector pLysS as the site for insertion of MCS (multiple cloning site), since the Tet ORF was already disrupted by the gene encoding T7 lysozyme, and tetracycline resistance gene is no longer functional. To keep the plasmid small for easy manipulation, we deleted a DNA fragment (715 bp) within the Tet ORF, from the unique SphI site to the STOP codon, and replaced it with a DNA fragment containing multiple cloning site which DNA sequence is as follows:

SEQ ID NO. 5:
gcatgccgatcgtcagcctgtcgactgcagtctagcactagtcgcga
SphI            SalI            SpeI ggtacctctgaggcgcgcctagtcatatg
KpnI      AscI        NdeI The plasmid map of pLysS MCS is shown in FIG. 3A. Sequence is SEQ ID NO. 6.

Example 3

The Construction of DPA2

Figure 3B:
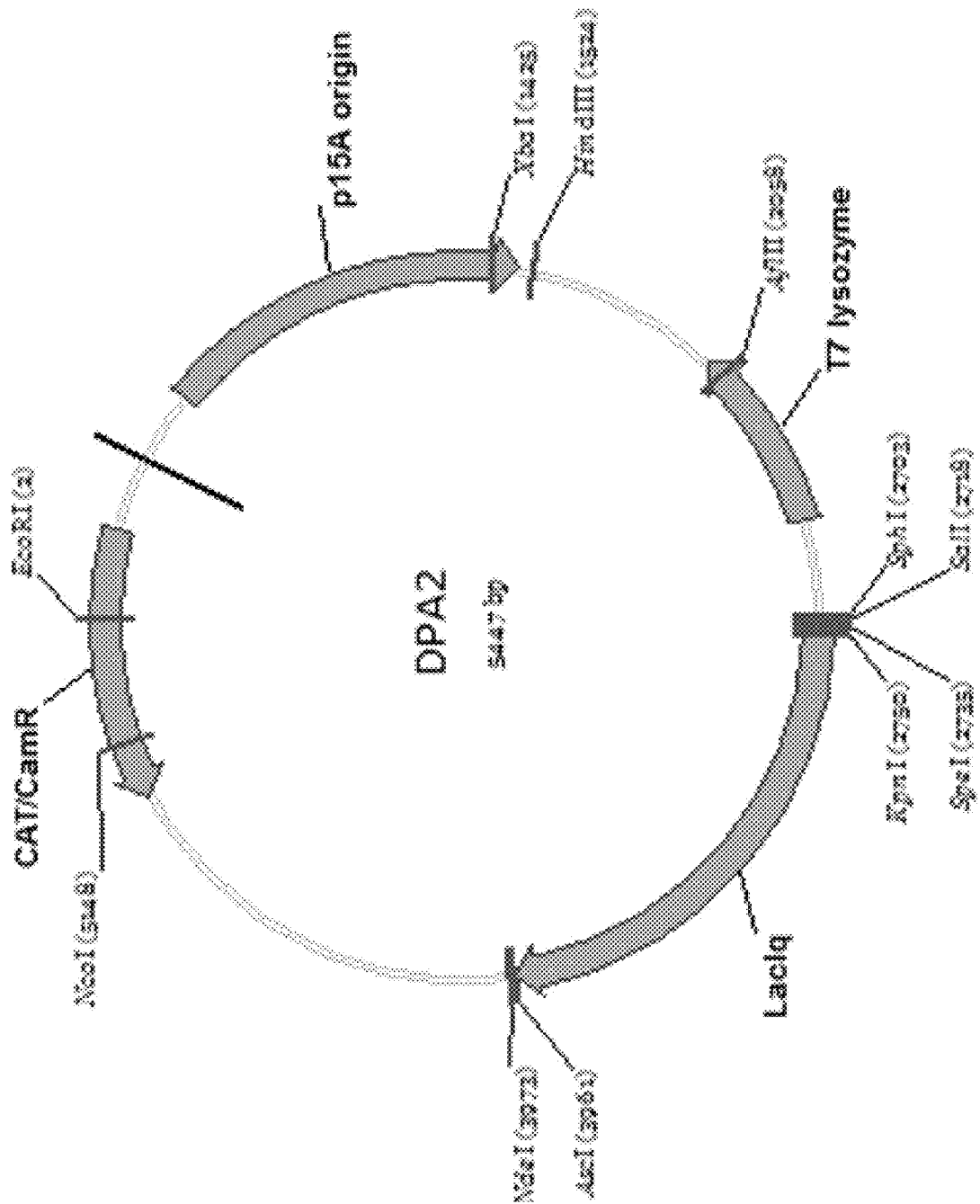

The plasmid DPA2 (dual plasmid autoinduction 2) is constructed by insertion of the gene lacI$^q$ between the unique KpnI and AscI sites within the multiple cloning sites of pLysS MCS. The transcription of lacI$^q$ is opposite to that of T7 lysozyme. The plasmid map of DPA2 is shown in FIG. 3B. Sequence is SEQ ID NO. 7. DPA2 contains a cryptic promoter that is likely to be constitutive. LacI$^q$ is expressed from DPA2 and is functional since in the absence of DPA2, DPA1 cannot be transformed into bacterial strains that do not have lacI$^q$ in F' factor (data not shown).

Example 4

The Autoinduction of Fabs Expressed from DPA1

The plasmid DPA2 was transformed into chemically competent E. coli strain TG1, and the transformed cells were prepared and stored at −80° C., into which DPA1 or its derivatives were then transformed. The transformants were selected on 2×YT plates (100 μg/ml Amp, 15 μg/ml CM and 1% Glucose).

We first determined the time course of autoinduction. As illustrated in Table 2, cultures continue to grow during the course of experiment, and A600 of overnight culture (21 hours) is generally higher than 7.0. Western blotting results (FIGS. 4A, 4B) clearly demonstrate that expression of two different target proteins, 4032 and 4119, are autoinduced, without addition of exogenous inducer, from about 4 hours after temperature shift when A600 is around 4.0 (Table 2). The amount of autoinduced proteins continue to accumulate, reaching higher levels in the overnight culture (21 hours).

TABLE 2

| $A_{600}$ | Time (hr) | | | | | |
|---|---|---|---|---|---|---|
| | 0 | 1 | 2.5 | 4 | 5.5 | 21 |
| 4032 | 0.6 | 1.4 | 2.55 | 3.94 | 4.2 | 7.1 |
| 4119 | 0.57 | 1.4 | 2.5 | 3.9 | 4.0 | 8.76 |

Figure 4A:
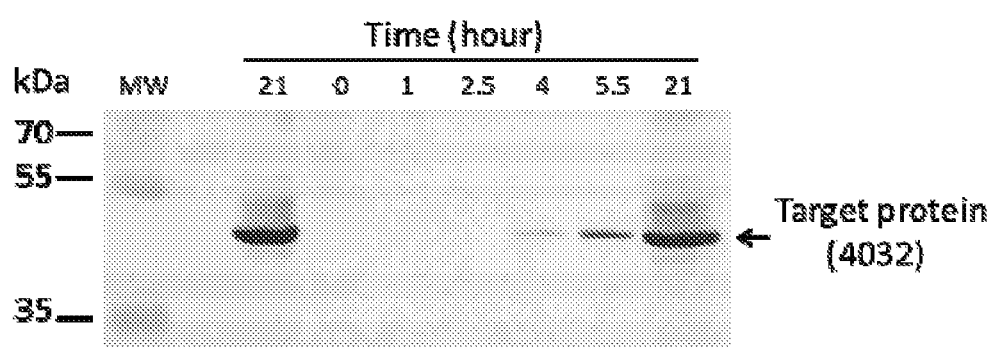
FIGS. 4A and 4B show expression of two different target proteins using an exemplary system of the present disclosure.
Figure 4B:
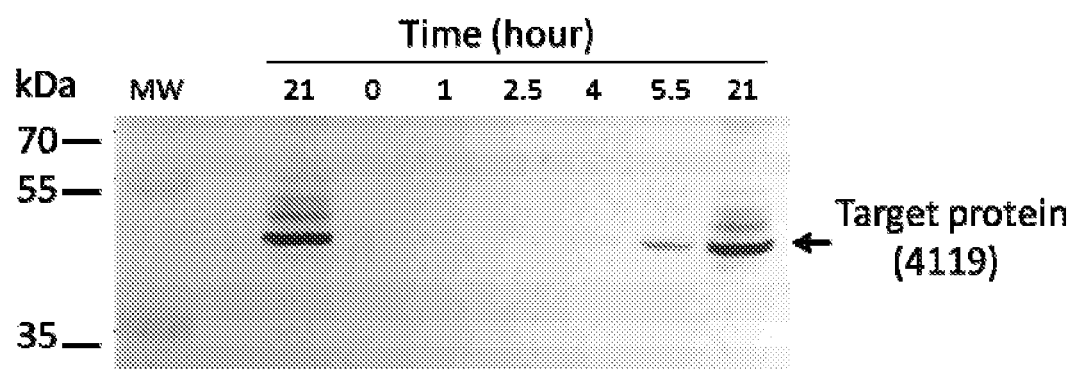

Experimental details for FIGS. 4A and 4B: plasmids DPA1-4032 or DPA1-4119 were separately transformed into chemically competent cells of TG1 containing the DPA2 plasmid, transformants were plated out on 2×YT plates (100 μg/ml Amp+, 15 μg/ml CM and 1% Glucose), and the plates were incubated at 37° C. overnight. Following morning single colonies were picked and inoculated into 5 ml of 2×YT medium (with 100 μg/ml Amp, 15 μg/ml CM and 1% Glucose), and grown at 37° C., 100 rpm overnight. Overnight cultures were inoculated into fresh Super Broth Medium (SB: 12 g Tryptone, 24 g Yeast Extract, 5 ml Glycerol, 3.81 g KH2PO4, 12.5 g K2HPO4, pH 7.0) so that A600 of the starting culture is 0.05. After about 2 hrs growth at 37° C., 250 rpm, A600 of the cultures reaches 0.6, and the culture temperature is adjusted to 22° C. to facilitate protein folding. Samples were taken out at different time points to monitor both culture growth, as well as expression induction through Western blotting.

Figure 5A:
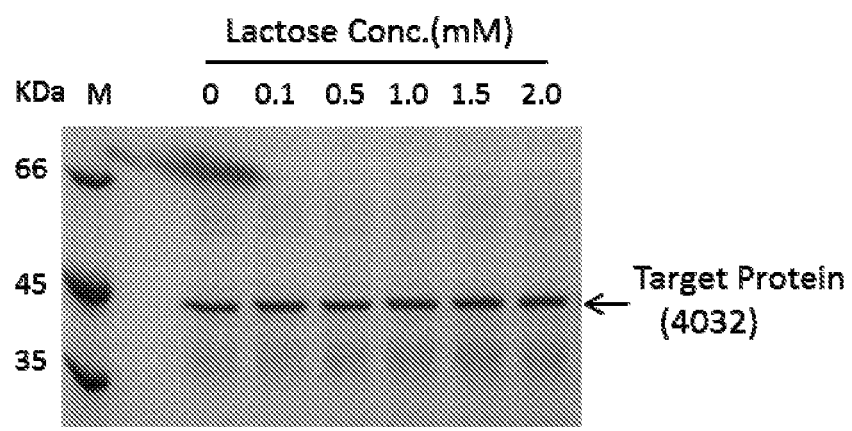
FIGS. 5A and 5B show effect of different amount of lactose (FIG. 5A) or IPTG (FIG. 5B) on expression using the system of the present disclosure.

We also tested whether addition of various concentrations of inducers, such as lactose or IPTG, can increase expression of our target proteins. As shown in FIG. 5A, addition of various concentrations of lactose in the medium does not increase target protein expression. As a matter of fact, addition of IPTG (1 mM) actually decreases the expression of our target protein (FIG. 5B).

Figure 5B:
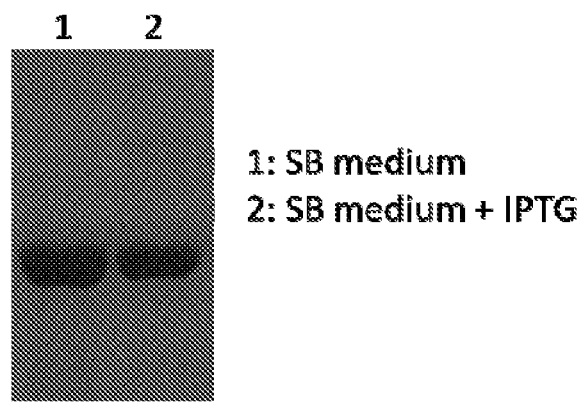

Experimental details for FIGS. 5A and 5B: bacterial transformant TG1 (containing DPA1-4032 and DPA2) was grown as above, the indicated final concentrations of lactose (FIG. 5A) or 1 mM IPTG (FIG. 5B) were added to culture medium after temperature shift. The same volume of overnight cultures was harvested, and the target proteins were eluted from Ni-NTA resin using the same volume of elution buffer. 5 μl of purified proteins were fractionated through 10% SDS-PAGE.

Figure 6:
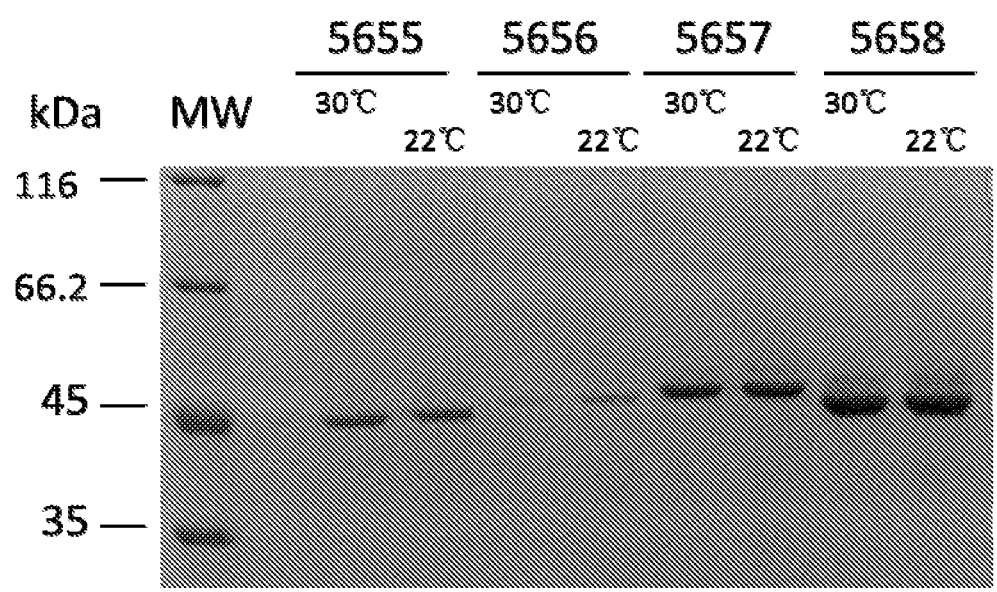
FIG. 6 shows expression using the system of the present disclosure without temperature shift.

We also tested our autoinduction system without temperature shift, i.e., the single colonies were inoculated into fresh SB medium and grew at 30° C. overnight, and then overnight cultures were harvested for protein purification. The results (FIG. 6) showed that for 3 (out of 4) samples, the protein yield remain unchanged. In one case, the yield is slightly lower when cultures were grown at 30° C. overnight. During all these experiments, no additional inducers were added into culture.

Therefore, we conclude that our dual plasmid autoinduction expression system does not require the addition of inducers, such as lactose or IPTG, for target protein expression. This system is highly useful for expression of proteins, especially for high-throughput protein expression where many samples will be processed in parallel.

We have used this autoinduction system in the expression of thousands of secreted Fabs generated from our phage display system with great efficiency. In addition, this system can be useful for expression of other membrane proteins or secreted proteins, since it has been shown that in conventional methods, fast transcription from strong promoters such as T7 promoter is detrimental to the host cell for membrane or secreted protein expression. Use of a weak Lac promoter and the autoinduction system of the present disclosure is predicted to be favorable for membrane or secreted protein expression.

Example 5

Combining Nuclease and Lysozyme into the DPA2 Plasmid

There are several other advantages for our Dual Plasmid Autoinduction (DPA) system. Since DPA2 is independent of the DPA1 plasmid that harbors target gene, it is convenient to add other features to it to further expand its usage, for example, to solve some problems encountered in downstream processes such as protein purification. We disclose here one such application, namely, the facilitation of cell lysate preparation through combination of two different enzymatic activities: the DNA-digesting nuclease activity and cell wall-digesting T7 lysozyme activities, both enzymes are encoded in the DPA2 plasmid.

Preparation of cell lysate is the first step in recombinant protein purification. It requires the breaking open bacterial cells and releasing cell content, which include mainly proteins and nucleic acid. The host-derived nucleic acid causes viscosity of cell lysates and contamination of final protein product (Boynton et al. (1999) Appl. Environ. Microbiol. 65(4):1524-1529; Cooke et al. (2003) J Biotechnol 101:229-239). Traditional way of reducing viscosity is through mechanical means such as sonication and mechanical shearing, both of which require specialized instruments and trained personnel. An alternative is to use purified nuclease, such as the popular Benzonase (U.S. Pat. No. 5,173,418 to Molin et al. (1992); Su et al. (2007) Journal of Immunological Methods 322: 94-103). However, the cost of the purified nuclease is quite significant when large number of samples have to be processed.

Figure 7A:
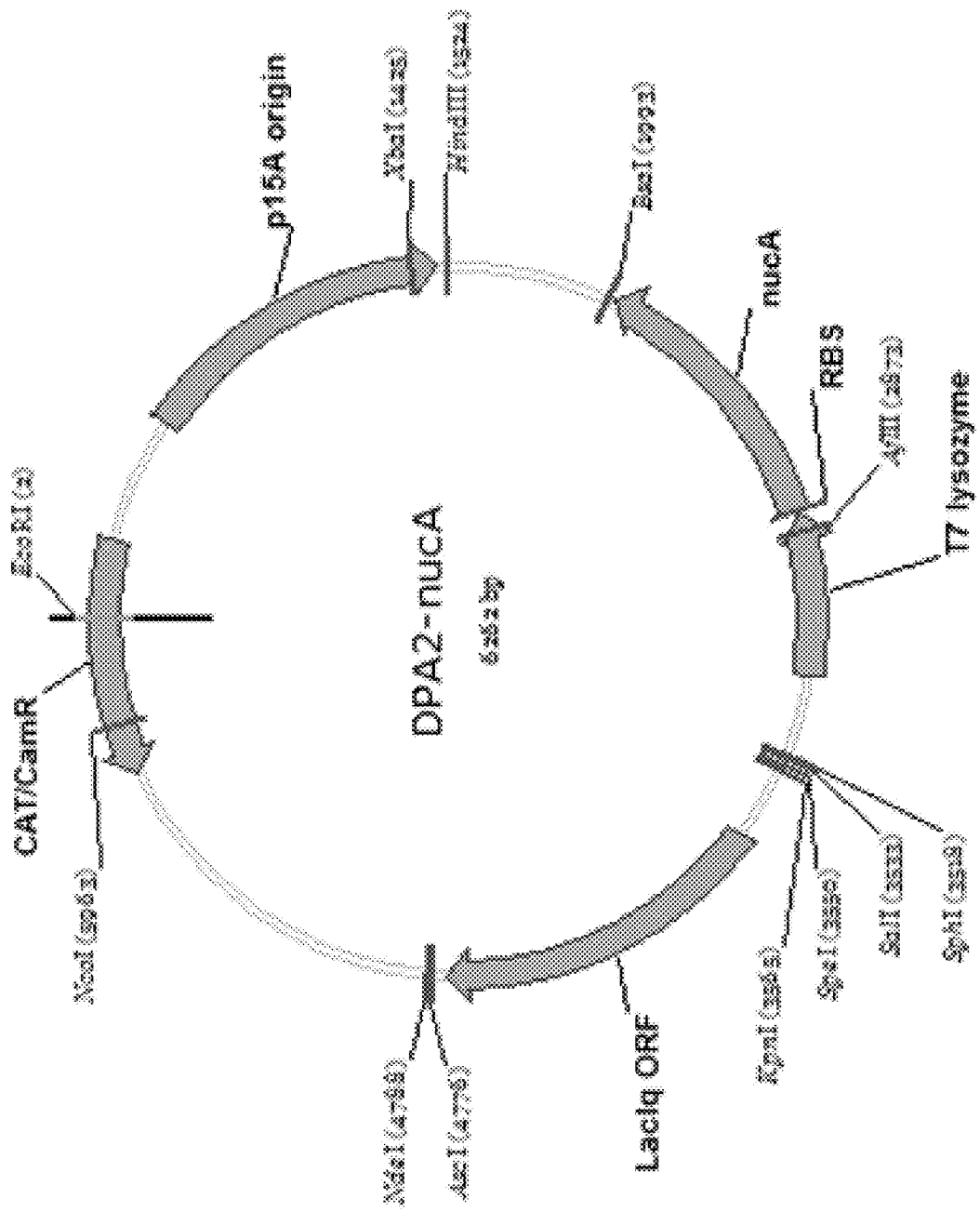
FIGS. 7A and 7B each provide a schematic map showing an exemplary plasmid of the present disclosure.
Figure 7B:
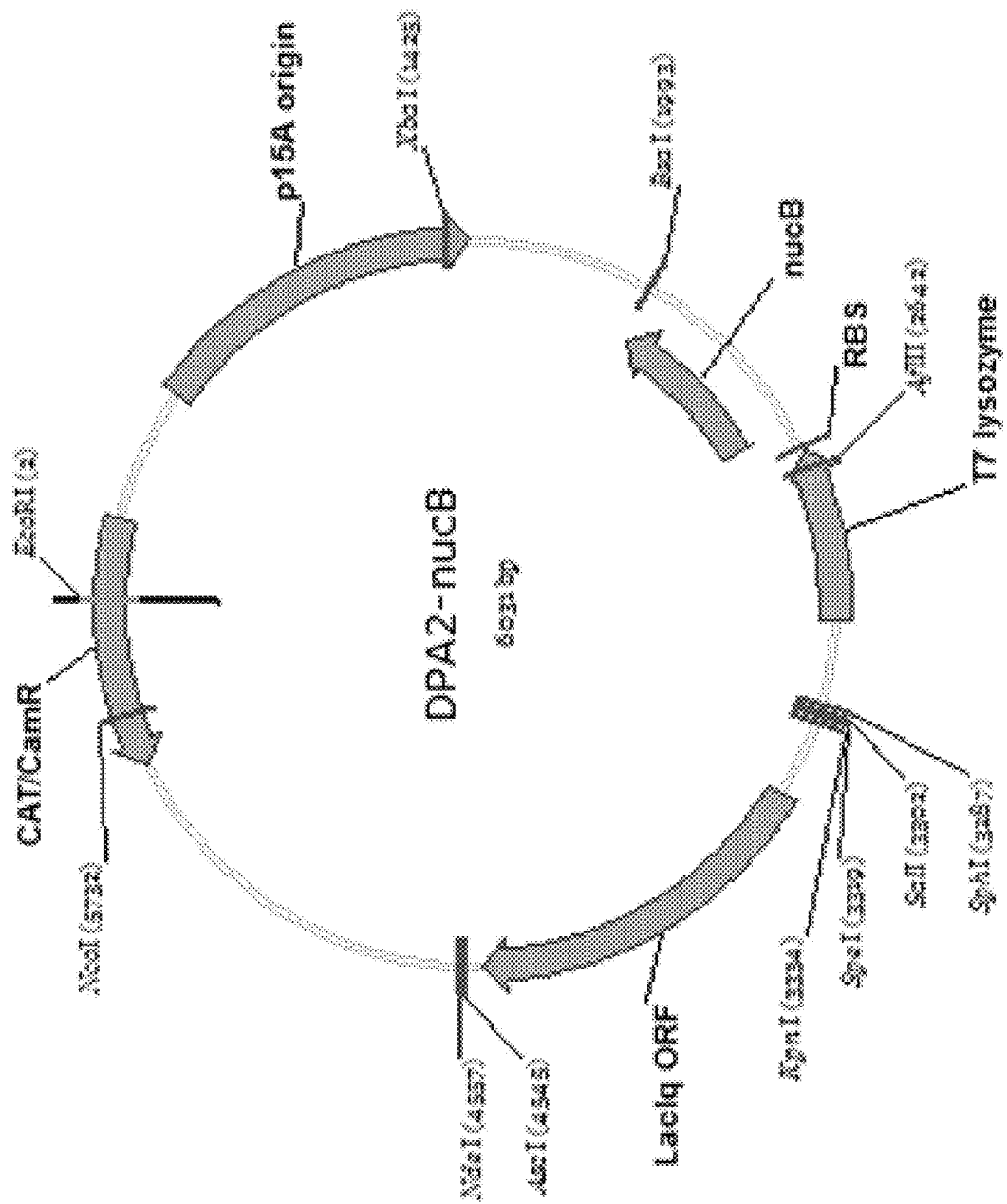

In this disclosure, we constructed DPA2-derived plasmids (DPA2-nucA and DPA2-nucB, map in FIGS. 7A and 7B, sequence in SEQ ID NOS. 8 and 9) that harbor genes encoding T7 lysozyme and two different nucleases (nucA and nucB). These two nucleases are commonly used. nucA is from *Serratia marcescens* while nucB is from *Staphylococcus aureus*. Both are non-specific nucleases that digest both DNA and RNA.

Figure 8A:
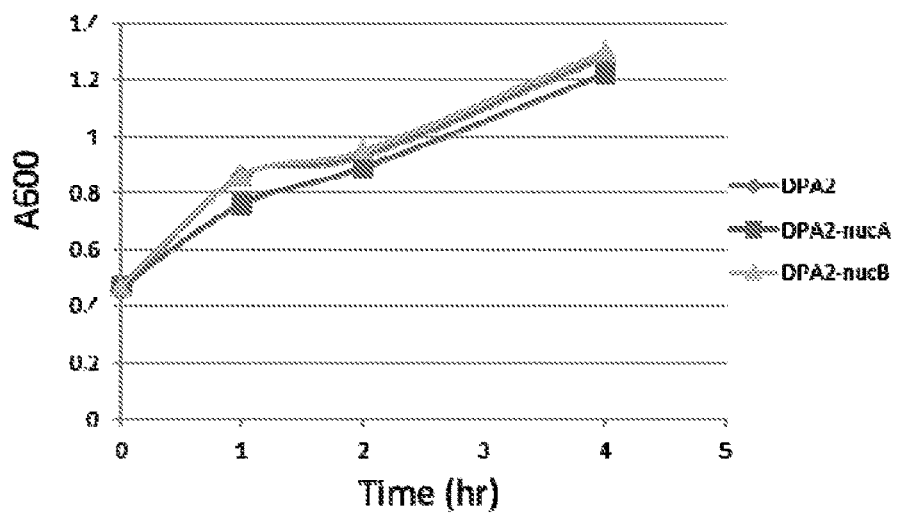
FIG. 8A shows effect of the plasmids of FIGS. 7A and 7B on the growth rate of the host cell.
Figure 8B:
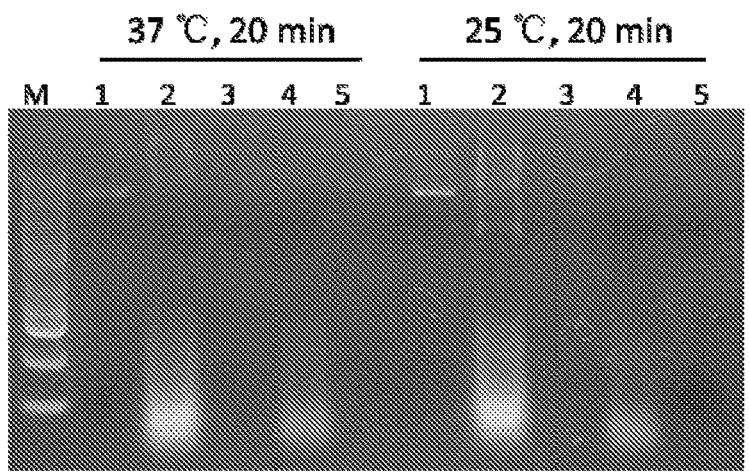
FIG. 8B shows digestion of chromosomal DNA and plasmid DNA by nuclease expressed from the plasmids of FIGS. 7A and 7B.

We showed that the presence of nuclease-encoding genes in DPA2 does not significantly affect the growth rate of the *E. coli* strains carrying these plasmids (FIG. 8A). Furthermore, through a single step of freezing and thawing, the released nucA or nucB nucleases were able to reduce the viscosity of cell lysate dramatically. From the agarose gel stained with nucleic acid dye DuGreen, it is obvious that both nucA and nucB were able to degrade chromosomal DNA and plasmid DNA to short DNA fragments (FIG. 8B, lanes 3 and 4). However, nucA worked more efficiently, and likely degraded chromosomal DNA and plasmid DNA to single nucleotide so that they are no longer visible in the gel (FIG. 8B, lane 3), similar to the effect of exogenously added purified Benzonase.

Figure 8C:
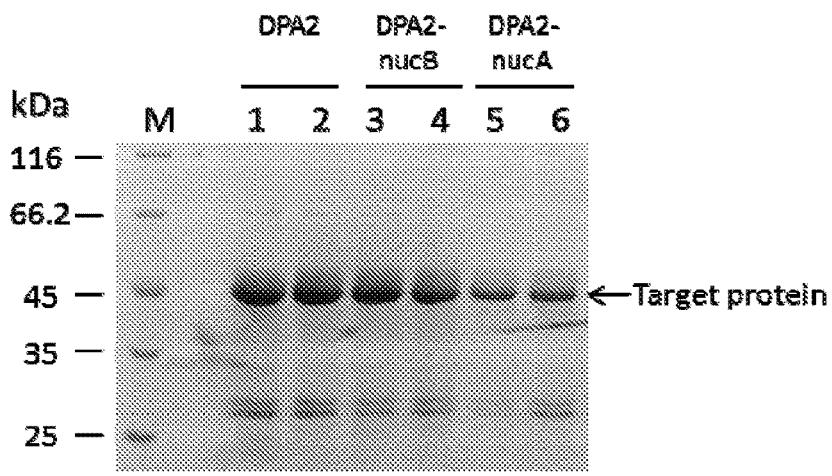
FIG. 8C shows expression of target protein using an exemplary system of the present disclosure.

We also tested whether the expression of nucA or nucB nucleases affected target protein expression, in this case, secreted Fab proteins. We found that Fab proteins encoded in DPA1 plasmids were still able to be expressed and secreted (FIG. 8C). However, their yields were negatively impacted by the expression of nucleases to different extent, with nucA more severely reduced final protein yield (FIG. 8C, lanes 5 and 6). It should be noted that in the two plasmids DPA2-nucA and DPA2-nucB, both nucleases are presumably constitutively expressed, which may affect host growth and expression of target protein. Introduction of inducible promoters to control expression of the nucleases (e.g., so that they are induced only in stationary phase) can circumvent issues encountered here, thereby increasing expression of target proteins.

FIG. 8A shows growth rate of *E. coli* strains carrying the DPA2 plasmids or its nuclease gene-containing derivatives DPA2-nucA and DPA2-nucB. The *E. coli* strain TG1 was cotransformed with two plasmids, the Fab-expressing plasmid DPA1-21Y or DPA2 (or its derivatives DPA2-nucA or DPA2-nucB). Overnight cultures of the transformants were inoculated (the starting A600 around 0.02) into fresh SB medium, and grown at 37° C., 200 rpm until A600 around 0.45. The temperature was then shifted to 22° C., and cultures were taken at different time points for the monitoring of growth rate. Overnight cultures were harvested for nuclease activity assay and protein purification.

Experimental details for FIG. 8B: Harvested cell pellets were resuspended in 5 volumes of lysis buffer A (50 mM Tris-HCl, 2 mM $MgCl_2$, pH 8.0), and then stored at −80° C. for 20 min. Afterwards samples were taken out and incubated in water bath at 25° C. or 37° C. for 20 min. The cell lysate in lane 2 was sonicated to reduce viscosity for easy pipetting. Benzonase (1 U/3 ml lysate) was added to the lysate in lane 5. The cell lysates were fractionated through 1% agarose gel and stained with nucleic acid stain DuGreen. Exogenous plasmid DNA (0.5 µg) was added to the lysates in lanes 2-5 as positive controls for nuclease activity. M: DNA ladder. Lane 1: purified plasmid DNA only. Lane 2: cell lysate from TG1 (DPA1-21Y+DPA2), sonicated. Lane 3: cell lysate from TG1 (DPA1-21Y+DPA2-nucA). Lane 4: cell lysate from TG1 (DPA1-21Y+DPA2-nucB). Lane 5: cell lysate from TG1 (DPA1-21Y+DPA2), purified Benzonase added.

Experimental details for FIG. 8C: bacterial transformants TG1 (DPA1-21Y+DPA2), TG1 (DPA1-21Y+DPA2-nucB, or TG1 (DPA1-21Y+DPA2-nucA) were grown as above. The same volume of overnight cultures was harvested, and the target proteins were eluted from Ni-NTA resin using the same volume of elution buffer. 5 µl of purified proteins were fractionated through 10% SDS-PAGE.

EQUIVALENTS

The present disclosure provides among other things novel methods and systems for autoinduction of protein expression, without the need to add an inducer. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and sequence database entries mentioned herein are hereby incorporated by reference in their entirety as if each individual publication or patent was specifically and individually indicated to be incorporated by reference.

The invention claimed is:

1. A bacterial cell for expression of a gene of interest, comprising:
   a first, high copy number genetic element comprising a gene of interest constructed to be under the control of an inducible promoter, wherein the gene of interest encodes a membrane protein or secreted protein, wherein the inducible promoter is a modified lac promoter that is devoid of any LacI open reading frame, and wherein the first genetic element is capable of replicating itself till at least 100 copies are present per cell; and
   a second, low copy number genetic element comprising a gene encoding LacI which, upon expression, represses transcription from the inducible promoter; wherein the second low copy number genetic element is not host chromosome or artificial chromosome, wherein the second genetic element is present at less than 20 copies per cell;
   wherein activation of transcription from the inducible promoter does not require addition of an exogenous inducer, and
   wherein the inducible promoter is induced by a trace amount of lactose that is insufficient to induce expression when glucose is present, and only activates expression when the glucose is depleted, and
   wherein the bacterial cell is an *E. coli* strain TG1 cell.

2. The bacterial cell of claim 1, wherein the first genetic element is a high copy number plasmid.

3. The bacterial cell of claim 2, wherein the high copy number plasmid is selected from the group consisting of: a pUC, pBluescript, and pGEM.

4. The bacterial cell of claim 1, wherein the gene of interest encodes an antibody fragment.

5. The bacterial cell of claim 1, wherein the first genetic element further comprises at least one transcriptional terminator.

6. The bacterial cell of claim 1, wherein the second genetic element is selected from the group consisting of: a low copy number plasmid, transposon, and episome.

7. The bacterial cell of claim 6, wherein the low copy number plasmid is selected from the group consisting of: pLysS, pR6K, pACYC, pSC101 and pWSK.

8. The bacterial cell of claim 1, wherein the second genetic element further comprises one or more genes selected from the group consisting of: a nuclease gene, a lysozyme gene, a chaperone gene and a biotin ligase gene.

9. A method for expressing a gene of interest, comprising culturing in a culture medium the bacterial cell of claim 1 for a sufficient period of time such that the gene of interest is expressed, wherein the culture medium comprises the trace amount of lactose endogenous therein.

10. The method of claim 9, further comprising autoinducing expression of the gene of interest by the trace amount of lactose endogenous in the culture medium.

11. The method of claim 9, wherein the sufficient period of time is about 4 hours or more.

12. The method of claim 9, further comprising expressing a nuclease for digesting chromosomal DNA of the bacterial cell.

13. The method of claim 9, further comprising expressing a lysozyme for digesting cell wall of the bacterial cell.

14. The method of claim 9, further comprising expressing a biotin ligase for biotinylation of a protein expressed from the gene of interest.

\* \* \* \* \*

SEQUENCE LISTING

```
<160> NUMBER OF SEQ ID NOS: 9

<210> SEQ ID NO 1
<211> LENGTH: 2644
<212> TYPE: DNA
<213> ORGANISM: Unknown
<220> FEATURE:
<223> OTHER INFORMATION: Artificial/synthetic sequence

<400> SEQUENCE: 1
```

```
gtggcacttt tcggggaaat gtgcgcggaa cccctatttg tttatttttc taaatacatt      60
caaatatgta tccgctcatg agacaataac cctgataaat gcttcaataa tattgaaaaa     120
ggaagagtat gagtattcaa catttccgtg tcgcccttat tccctttttt gcggcatttt     180
gccttcctgt ttttgctcac ccagaaacgc tggtgaaagt aaaagatgct gaagatcagt     240
tgggtgcacg agtgggttac atcgaactgg atctcaacag cggtaagatc cttgagagtt     300
ttcgccccga agaacgtttc ccaatgatga gcacttttaa agttctgcta tgtggcgcgg     360
tattatcccg tattgacgcc gggcaagagc aactcggtcg ccgcatacac tattctcaga     420
atgacttggt tgagtactca ccagtcacag aaaagcatct tacgatggc atgacagtaa      480 gagaattatg cagtgctgcc ataaccatga gtgataacac tgcggccaac ttacttctga     540
caacgattgg aggaccgaag gagctaaccg cttttttgca caacatgggg gatcatgtaa     600
ctcgccttga tcgttgggaa ccggagctga atgaagccat accaaacgac gagcgtgaca     660
ccacgatgcc tgtagcaatg gcaacaacgt tgcgcaaact attaactggc gaactactta     720
ctctagcttc ccggcaacaa ttaatagact ggatggaggc ggataaagtt gcaggaccac     780
ttctgcgctc ggcccttccg gctggctggt ttattgctga taaatctgga gccggtgagc     840
gtgggtctcg cggtatcatt gcagcactgg ggccagatgg taagccctcc cgtatcgtag     900
ttatctacac gacggggagt caggcaacta tggatgaacg aaatagacag atcgctgaga     960
taggtgcctc actgattaag cattggtaac tgtcagacca agtttactca tatatacttt    1020
agattgattt aaaacttcat ttttaattta aaaggatcta ggtgaagatc ctttttgata    1080
atctcatgac caaaatccct taacgtgagt tttcgttcca ctgagcgtca gaccccgtag    1140
aaaagatcaa aggatcttct tgagatcctt ttttctgcg cgtaatctgc tgcttgcaaa     1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag cgcagcggt cgggctgaac ggggggttcg tgcacacagc     1500
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatggaaaaa cgccagcaac gcggcctttt tacggttcct ggccttttgc tggccttttg    1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga ggcctgcacg gccgtacccg ataaaagcgg cttcctgaca ggaggccgtt    1980
ttgttttgca gcccacctac gcgtgcgcaa cgcaattaat gtgagttagc tcactcatta    2040
ggcaccccag gctttacact ttatgcttcc ggctcgtatg ttgtgtggaa ttgtgagcgg    2100
ataacaattt cacacaaagg agatatacat atgtctagat aataagctcg gttgccgccg    2160
ggcgtttttt atggccaaac aggccgacgc gccctgtagc ggcgcattaa gcgcggcggg    2220
tgtggtggtt acgcgcagcg tgaccgctac acttgccagc gccctagcgc ccgctccttt    2280
cgctttcttc ccttcctttc tcgccacgtt cgccggcttt ccccgtcaag ctctaaatcg    2340
```

| | |
|---|---|
| ggggctccct ttagggttcc gatttagtgc tttacggcac ctcgacccca aaaaacttga | 2400 |
| ttagggtgat ggttcacgta gtgggccatc gccctgatag acggttttc gccctttgac | 2460 |
| gttggagtcc acgttcttta atagtggact cttgttccaa actggaacaa cactcaaccc | 2520 |
| tatctcggtc tattcttttg atttataagg gattttgccg atttcggcct attggttaaa | 2580 |
| aaatgagctg atttaacaaa aatttaacgc gaattttaac aaaatattaa cgcttacaat | 2640 |
| ttag | 2644 |

<210> SEQ ID NO 2
<211> LENGTH: 55
<212> TYPE: DNA
<213> ORGANISM: Unknown
<220> FEATURE:
<223> OTHER INFORMATION: Artifitial/synthetic sequence

<400> SEQUENCE: 2

| | |
|---|---|
| gtacccgata aaagcggctt cctgacagga ggccgttttg ttttgcagcc cacct | 55 |

<210> SEQ ID NO 3
<211> LENGTH: 112
<212> TYPE: DNA
<213> ORGANISM: Unknown
<220> FEATURE:
<223> OTHER INFORMATION: Artificial/synthetic sequence

<400> SEQUENCE: 3

| | |
|---|---|
| gcgcaacgca attaatgtga gttagctcac tcattaggca ccccaggctt tacactttat | 60 |
| gcttccggct cgtatgttgt gtggaattgt gagcggataa caatttcaca ca | 112 |

<210> SEQ ID NO 4
<211> LENGTH: 27
<212> TYPE: DNA
<213> ORGANISM: Unknown
<220> FEATURE:
<223> OTHER INFORMATION: Artificial/synthetic sequence

<400> SEQUENCE: 4

| | |
|---|---|
| gctcggttgc cgccgggcgt tttttat | 27 |

<210> SEQ ID NO 5
<211> LENGTH: 76
<212> TYPE: DNA
<213> ORGANISM: Unknown
<220> FEATURE:
<223> OTHER INFORMATION: Artificial/synthetic sequence

<400> SEQUENCE: 5

| | |
|---|---|
| gcatgccgat cgtcagcctg tcgactgcag tctagcacta gtcgcgaggt acctctgagg | 60 |
| cgcgcctagt catatg | 76 |

<210> SEQ ID NO 6
<211> LENGTH: 4244
<212> TYPE: DNA
<213> ORGANISM: Unknown
<220> FEATURE:
<223> OTHER INFORMATION: Artificial/synthetic sequence

<400> SEQUENCE: 6

| | |
|---|---|
| gaattccgga tgagcattca tcaggcgggc aagaatgtga ataaaggccg gataaaactt | 60 |
| gtgcttattt ttctttacgg tctttaaaaa ggccgtaata tccagctgaa cggtctggtt | 120 |
| ataggtacat tgagcaactg actgaaatgc ctcaaaatgt tctttacgat gccattggga | 180 |

```
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgccccctg acaagcatca cgaaatctga cgctcaaatc    900
agtggtggcg aaacccgaca ggactataaa gataccaggc gtttccctg gcggctccct    960 cgtgcgctct cctgttcctg cctttcggtt taccggtgtc attccgctgt tatggccgcg   1020
tttgtctcat tccacgcctg acactcagtt ccgggtaggc agttcgctcc aagctggact   1080
gtatgcacga accccccgtt cagtccgacc gctgcgcctt atccggtaac tatcgtcttg   1140
agtccaaccc ggaaagacat gcaaaagcac cactggcagc agccactggt aattgattta   1200
gaggagttag tcttgaagtc atgcgccggt taaggctaaa ctgaaaggac aagttttggt   1260
gactgcgctc ctccaagcca gttacctcgg ttcaaagagt tggtagctca gagaaccttc   1320
gaaaaaccgc cctgcaaggc ggttttttcg ttttcagagc aagagattac gcgcagacca   1380
aaacgatctc aagaagatca tcttattaat cagataaaat atttctagat ttcagtgcaa   1440
tttatctctt caaatgtagc acctgaagtc agccccatac gatataagtt gtaattctca   1500
tgtttgacag cttatcatcg ataagcttta atgcggtagt ttatcacagt taaattgcta   1560
acgcagtcag gcaccgtgta tgaaatctaa caatgcgctc atcgtcatcc tcggcaccgt   1620
caccctggat gctgtaggca taggcttggt tatgccggta ctgccgggcc tcttgcggga   1680
tatcgtccat tccgacagca tcgccagtca ctatggcgtg ctgctagcgc tatatgcgtt   1740
gatgcaattt ctatgcgcac ccgttctcgg agcactgtcc gaccgctttg gccgccgccc   1800
agtcctgctc gcttcgctac ttggagccac tatcgactac gcgatcatgg cgaccacacc   1860
cgtcctgtgg atccggccca ttggctgcct cccacacttg gatatgcctc ctcggagcct   1920
tatagaattg tttataagac ttgcgcatta tttgacctcc aatgcgaaca aagggaaacc   1980
gctgtggtct ccctttagtg agttcaatta attatccacg gtcagaagtg accagttcgt   2040
tcttctccca ccaacgctta aggtcgaacg aagggcaagc cttcggcgcc acctcatgat   2100
gggcgcgaag accagcgcct tcgtacttag ccagcagtgt gacaagcagt gagcgaaggg   2160
attgcatttg ggctggcgta aagttagcgt cgaacttacc tttatcgtcg ataccaccaa   2220
caaggcagac gccgatagag ttgtggttgt aacccttagc gtgagagcct acagccatct   2280
catctcgtcc tgcctccaca gtaccgtctc gcttgatgat aaagtggtat cccacatcga   2340
gccaaccctg ctctttgtgc cactggcgaa tctcacggac accaacattc tgacttggct   2400
tggtagccga gcagtgaaca aagattgcgt cagtagattc acgttgttta aactgtacac   2460
gagccattat ttctttcctc ctttcctttt taatctatca aaggggaccc ggatcctcta   2520
```

```
cgccggacgc atcgtggccg gcatcaccgg cgccacaggt gcggttgctg gcgcctatat    2580
cgccgacatc accgatgggg aagatcgggc tcgccacttc gggctcatga gcgcttgttt    2640
cggcgtgggt atggtggcag gccccgtggc cgggggactg ttgggcgcca tctccttgca    2700
tgccgatcgt cagcctgtcg actgcagtct agcactagtc gcgaggtacc tctgaggcgc    2760
gcctagtcat atggaagccg gcggcacctc gctaacggat tcaccactcc aagaattgga    2820
gccaatcaat tcttgcggag aactgtgaat gcgcaaacca accttggca gaacatatcc     2880 atcgcgtccg ccatctccag cagccgcacg cggcgcatct cgggcagcgt gggtcctgg     2940 ccacgggtgc gcatgatcgt gctcctgtcg ttgaggaccc ggctaggctg gcggggttgc    3000
cttactggtt agcagaatga atcaccgata cgcgagcgaa cgtgaagcga ctgctgctgc    3060
aaaacgtctg cgacctgagc aacaacatga atggtcttcg gtttccgtgt ttcgtaaagt    3120
ctggaaacgc ggaagtcccc tacgtgctgc tgaagttgcc cgcaacagag agtggaacca    3180
accggtgata ccacgatact atgactgaga gtcaacgcca tgagcggcct catttcttat    3240
tctgagttac aacagtccgc accgctgtcc ggtagctcct tccggtgggc gcggggcatg    3300
actatcgtcg ccgcacttat gactgtcttc tttatcatgc aactcgtagg acaggtgccg    3360
gcagcgccca acagtccccc ggccacgggg cctgccacca tacccacgcc gaaacaagcg    3420
ccctgcacca ttatgttccg gatctgcatc gcaggatgct gctggctacc ctgtggaaca    3480
cctacatctg tattaacgaa gcgctaaccg ttttttatcag gctctgggag gcagaataaa   3540
tgatcatatc gtcaattatt acctccacgg ggagagcctg agcaaactgg cctcaggcat    3600
ttgagaagca cacggtcaca ctgcttccgg tagtcaataa accggtaaac cagcaataga    3660
cataagcggc tatttaacga ccctgccctg aaccgacgac cgggtcgaat ttgctttcga    3720
atttctgcca ttcatccgct tattatcact tattcaggcg tagcaccagg cgtttaaggg    3780
caccaataac tgccttaaaa aaattacgcc ccgccctgcc actcatcgca gtactgttgt    3840
aattcattaa gcattctgcc gacatggaag ccatcacaga cggcatgatg aacctgaatc    3900
gccagcggca tcagcacctt gtcgccttgc gtataatatt tgcccatggt gaaaacgggg    3960
gcgaagaagt tgtccatatt ggccacgttt aaatcaaaac tggtgaaact cacccaggga    4020
ttggctgaga cgaaaaacat attctcaata aacccttag ggaaataggc caggttttca     4080
ccgtaacacg ccacatcttg cgaatatatg tgtagaaact gccggaaatc gtcgtggtat    4140
tcactccaga gcgatgaaaa cgtttcagtt tgctcatgga aaacggtgta acaagggtga    4200
acactatccc atatcaccag ctcaccgtct ttcattgcca tacg                     4244
```

<210> SEQ ID NO 7
<211> LENGTH: 5447
<212> TYPE: DNA
<213> ORGANISM: Unknown
<220> FEATURE:
<223> OTHER INFORMATION: Artificial/synthetic sequence

<400> SEQUENCE: 7

```
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt attcattat ggtgaaagtt      300 ggaacctctt acgtgccgat caacgtctca ttttcgccaa agttggccc agggcttccc     360
```

```
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgccccctg acaagcatca cgaaatctga cgctcaaatc    900
agtggtggcg aaacccgaca ggactataaa gataccaggc gtttccctg gcggctccct    960 cgtgcgctct cctgttcctg cctttcggtt taccggtgtc attccgctgt tatggccgcg   1020
tttgtctcat tccacgcctg acactcagtt ccgggtaggc agttcgctcc aagctggact   1080
gtatgcacga accccccgtt cagtccgacc gctgcgcctt atccggtaac tatcgtcttg   1140
agtccaaccc ggaaagacat gcaaaagcac cactggcagc agccactggt aattgattta   1200
gaggagttag tcttgaagtc atgcgccggt taaggctaaa ctgaaaggac aagttttggt   1260
gactgcgctc ctccaagcca gttacctcgg ttcaaagagt tggtagctca gagaaccttc   1320 gaaaaccgc cctgcaaggc ggttttttcg ttttcagagc aagagattac gcgcagacca   1380
aaacgatctc aagaagatca tcttattaat cagataaaat atttctagat ttcagtgcaa   1440
tttatctctt caaatgtagc acctgaagtc agccccatac gatataagtt gtaattctca   1500
tgtttgacag cttatcatcg ataagcttta atgcggtagt ttatcacagt taaattgcta   1560
acgcagtcag gcaccgtgta tgaaatctaa caatgcgctc atcgtcatcc tcggcaccgt   1620
caccctggat gctgtaggca taggcttggt tatgccggta ctgccgggcc tcttgcggga   1680
tatcgtccat tccgacagca tcgccagtca ctatggcgtg ctgctagcgc tatatgcgtt   1740
gatgcaattt ctatgcgcac ccgttctcgg agcactgtcc gaccgctttg gccgccgccc   1800
agtcctgctc gcttcgctac ttggagccac tatcgactac gcgatcatgg cgaccacacc   1860
cgtcctgtgg atccggccca ttggctgcct cccacacttg gatatgcctc ctcggagcct   1920
tatagaattg tttataagac ttgcgcatta tttgacctcc aatgcgaaca aagggaaacc   1980
gctgtggtct ccctttagtg agttcaatta attatccacg gtcagaagtg accagttcgt   2040
tcttctccca ccaacgctta aggtcgaacg aagggcaagc cttcggcgcc acctcatgat   2100
gggcgcgaag accagcgcct tcgtacttag ccagcagtgt gacaagcagt gagcgaaggg   2160
attgcatttg ggctggcgta aagttagcgt cgaacttacc tttatcgtcg ataccaccaa   2220
caaggcagac gccgatagag ttgtggttgt aacccttagc gtgagagcct acagccatct   2280
catctcgtcc tgcctccaca gtaccgtctc gcttgatgat aaagtggtat cccacatcga   2340
gccaaccctg ctctttgtgc cactggcgaa tctcacggac accaacattc tgacttggct   2400
tggtagccga gcagtgaaca aagattgcgt cagtagattc acgttgttta aactgtacac   2460
gagccattat ttctttcctc ctttccttt taatctatca aaggggaccc ggatcctcta   2520
cgccggacgc atcgtggccg gcatcaccgg cgccacaggt gcggttgctg cgcctatat   2580 cgccgacatc accgatgggg aagatcgggc tcgccacttc gggctcatga gcgcttgttt   2640
cggcgtgggt atggtggcag gccccgtggc cgggggactg ttgggcgcca tctccttgca   2700
```

```
tgccgatcgt cagcctgtcg actgcagtct agcactagtc gcgaggtacc attccgacac    2760
catcgaatgg tgcaaaacct ttcgcggtat ggcatgatag cgcccggaag agagtcaatt    2820
cagggtggtg aatgtgaaac cagtaacgtt atacgatgtc gcagagtatg ccggtgtctc    2880
ttatcagacc gtttcccgcg tggtgaacca ggccagccac gtttctgcga aaacgcggga    2940
aaaagtggaa gcggcgatgg cggagctgaa ttacattccc aaccgcgtgg cacaacaact    3000
ggcgggcaaa cagtcgttgc tgattggcgt tgccacctcc agtctggccc tgcacgcgcc    3060
gtcgcaaatt gtcgcggcga ttaaatctcg cgccgatcaa ctgggtgcca gcgtggtggt    3120
gtcgatggta gaacgaagcg gcgtcgaagc ctgtaaagcg gcggtgcaca atcttctcgc    3180
gcaacgcgtc agtgggctga tcattaacta tccgctggat gaccaggatg ccattgctgt    3240
ggaagctgcc tgcactaatg ttccggcgtt atttcttgat gtctctgacc agacacccat    3300
caacagtatt attttctccc atgaagacgg tacgcgactg ggcgtggagc atctggtcgc    3360
attgggtcac cagcaaatcg cgctgttagc gggcccatta agttctgtct cggcgcgtct    3420
gcgtctggct ggctggcata aatatctcac tcgcaatcaa attcagccga tagcggaacg    3480
ggaaggcgac tggagtgcca tgtccggttt tcaacaaacc atgcaaatgc tgaatgaggg    3540
catcgttccc actgcgatgc tggttgccaa cgatcagatg gcgctgggcg caatgcgcgc    3600
cattaccgag tccgggctgc gcgttggtgc ggatatctcg gtagtgggat acgacgatac    3660
cgaagacagc tcatgttata tcccgccgtc aaccaccatc aaacaggatt ttcgcctgct    3720
ggggcaaacc agcgtggacc gcttgctgca actctctcag ggccaggcgg tgaagggcaa    3780
tcagctgttg cccgtctcac tggtgaaaag aaaaaccacc ctggcgccca atacgcaaac    3840
cgcctctccc cgcgcgttgg ccgattcatt aatgcagctg gcacgacagg tttcccgact    3900
ggaaagcggg cagtgagcgc aacgcaatta atgtgagtta gctcactcat taggcaccgg    3960
cgcgcctagt catatggaag ccggcggcac ctcgctaacg gattcaccac tccaagaatt    4020
ggagccaatc aattcttgcg gagaactgtg aatgcgcaaa ccaacccttg gcagaacata    4080
tccatcgcgt ccgccatctc cagcagccgc acgcggcgca tctcgggcag cgttgggtcc    4140
tggccacggg tgcgcatgat cgtgctcctg tcgttgagga cccggctagg ctggcggggt    4200
tgccttactg gttagcagaa tgaatcaccg atacgcgagc gaacgtgaag cgactgctgc    4260
tgcaaaacgt ctgcgacctg agcaacaaca tgaatggtct tcggtttccg tgtttcgtaa    4320
agtctggaaa cgcggaagtc ccctacgtgc tgctgaagtt gcccgcaaca gagagtggaa    4380
ccaaccggtg ataccacgat actatgactg agagtcaacg ccatgagcgg cctcatttct    4440
tattctgagt tacaacagtc cgcaccgctg tccggtagct ccttccggtg ggcgcggggc    4500
atgactatcg tcgccgcact tatgactgtc ttctttatca tgcaactcgt aggacaggtg    4560
ccggcagcgc ccaacagtcc cccggccacg gggcctgcca ccatacccac gccgaaacaa    4620
gcgccctgca ccattatgtt ccggatctgc atcgcaggat gctgctggct accctgtgga    4680
acacctacat ctgtattaac gaagcgctaa ccgttttat caggctctgg gaggcagaat    4740
aaatgatcat atcgtcaatt attacctcca cggggagagc ctgagcaaac tggcctcagg    4800
catttgagaa gcacacggtc acactgcttc cggtagtcaa taaaccggta aaccagcaat    4860
agacataagc ggctatttaa cgaccctgcc ctgaaccgac gaccgggtcg aatttgcttt    4920
cgaatttctg ccattcatcc gcttattatc acttattcag gcgtagcacc aggcgtttaa    4980
gggcaccaat aactgcctta aaaaaattac gccccgccct gccactcatc gcagtactgt    5040
tgtaattcat taagcattct gccgacatgg aagccatcac agacggcatg atgaacctga    5100
```

| | | |
|---|---|---|
| atcgccagcg gcatcagcac cttgtcgcct tgcgtataat atttgcccat ggtgaaaacg | 5160 |
| ggggcgaaga agttgtccat attggccacg tttaaatcaa aactggtgaa actcacccag | 5220 |
| ggattggctg agacgaaaaa catattctca ataaacccctt tagggaaata ggccaggttt | 5280 |
| tcaccgtaac acgccacatc ttgcgaatat atgtgtagaa actgccggaa atcgtcgtgg | 5340 |
| tattcactcc agagcgatga aaacgtttca gtttgctcat ggaaaacggt gtaacaaggg | 5400 |
| tgaacactat cccatatcac cagctcaccg tctttcattg ccatacg | 5447 |

<210> SEQ ID NO 8
<211> LENGTH: 6262
<212> TYPE: DNA
<213> ORGANISM: Unknown
<220> FEATURE:
<223> OTHER INFORMATION: Artificial/synthetic sequence

<400> SEQUENCE: 8

| | | |
|---|---|---|
| gaattccgga tgagcattca tcaggcgggc aagaatgtga ataaaggccg gataaaactt | 60 |
| gtgcttattt ttctttacgg tctttaaaaa ggccgtaata tccagctgaa cggtctggtt | 120 |
| ataggtacat tgagcaactg actgaaatgc ctcaaaatgt tctttacgat gccattggga | 180 |
| tatatcaacg gtggtatatc cagtgatttt tttctccatt ttagcttcct tagctcctga | 240 |
| aaatctcgat aactcaaaaa atacgcccgg tagtgatctt atttcattat ggtgaaagtt | 300 |
| ggaacctctt acgtgccgat caacgtctca ttttcgccaa aagttggccc agggcttccc | 360 |
| ggtatcaaca gggacaccag gatttatttta ttctgcgaag tgatcttccg tcacaggtat | 420 |
| ttattcggcg caaagtgcgt cgggtgatgc tgccaactta ctgatttagt gtatgatggt | 480 |
| gtttttgagg tgctccagtg gcttctgttt ctatcagctg tccctcctgt tcagctactg | 540 |
| acggggtggt gcgtaacggc aaaagcaccg ccggacatca gcgctagcgg agtgtatact | 600 |
| ggcttactat gttggcactg atgagggtgt cagtgaagtg cttcatgtgg caggagaaaa | 660 |
| aaggctgcac cggtgcgtca gcagaatatg tgatacagga tatattccgc ttcctcgctc | 720 |
| actgactcgc tacgctcggt cgttcgactg cggcgagcgg aaatggctta cgaacggggc | 780 |
| ggagatttcc tggaagatgc caggaagata cttaacagga agtgagagg gccgcggcaa | 840 |
| agccgttttt ccataggctc cgcccccctg acaagcatca cgaaatctga cgctcaaatc | 900 |
| agtggtggcg aaacccgaca ggactataaa gataccaggc gtttccctg gcggctccct | 960 |
| cgtgcgctct cctgttcctg cctttcggtt taccggtgtc attccgctgt tatggccgcg | 1020 |
| tttgtctcat tccacgcctg acactcagtt ccgggtaggc agttcgctcc aagctggact | 1080 |
| gtatgcacga accccccgtt cagtccgacc gctgcgcctt atccggtaac tatcgtcttg | 1140 |
| agtccaaccc ggaaagacat gcaaaagcac cactggcagc agccactggt aattgattta | 1200 |
| gaggagttag tcttgaagtc atgcgccggt taaggctaaa ctgaaaggac aagttttggt | 1260 |
| gactgcgctc ctccaagcca gttacctcgg ttcaaagagt tggtagctca gagaaccttc | 1320 |
| gaaaaaccgc cctgcaaggc ggttttttcg ttttcagagc aagagattac gcgcagacca | 1380 |
| aaacgatctc aagaagatca tcttattaat cagataaaat atttctagat ttcagtgcaa | 1440 |
| tttatctctt caaatgtagc acctgaagtc agccccatac gatataagtt gtaattctca | 1500 |
| tgtttgacag cttatcatcg ataagcttta atgcggtagt ttatcacagt taaattgcta | 1560 |
| acgcagtcag gcaccgtgta tgaaatctaa caatgcgctc atcgtcatcc tcggcaccgt | 1620 |
| caccctggat gctgtaggca taggcttggt tatgccggta ctgccgggcc tcttgcggga | 1680 |

-continued

```
tatcgtccat tccgacagca tcgccagtca ctatggcgtg ctgctagcgc tatatgcgtt    1740
gatgcaattt ctatgcgcac ccgttctcgg agcactgtcc gaccgctttg ccgccgccc     1800 agtcctgctc gcttcgctac ttggagccac tatcgactac gcgatcatgg cgaccacacc    1860
cgtcctgtgg atccgcccca ttggctgcct cccacacttg gatatgcctc ctcggagcct    1920
tatagaattg tttataagac ttgcgcatta tttgacctcc aatgcgaaca aagggaaacc    1980
gctgtggtct ccctttagtg agttcaatta atcagttttt gcagcccatc aactccggca    2040
gaacgcccgg tttgctcttc agcgaagcct gcacgtcgtc cggcagaccg cccagatga    2100 tcaggccggt gcgtttctcg atctcgtcca ccgtcacgcg gaattggcag aaatcggcgc    2160
ccttcggcgt gttctggtcg aacaggaagg cggcatagtg gttcaccgcc gggctgttgt    2220
tgatgaaaat taccttccag taggcgctgg ggatggtgtg cgctttctgg gtgcccggca    2280
gtttgcccat atcgcgctca tacagcggcc cggtcacggt atagaccgag gagatatcgg    2340
cgcgatcgat cagcttgcgt tcctgatctt ccagccgagc ccaggcgccc tggttcagat    2400
cggacttttg cggcgtgatg ttggacaggt agttcaacga ttcccagtcg gaaacgcccg    2460
ccagcgaggc cagcggcgcc tgatgaccgc gatcgacctt cagcgcggcg ttggcaccgg    2520
tgtaatcggg gggcgccaga gtgtccgccg gattgagagc cggatcggtt ttccagttgc    2580
gcgtcttgcc gctggccggc gtgtctttgg tgatgtgata ggccacccag ttggcgaact    2640
tggtggtgct gttgttgttc aacgtataag catggcgcac gatagacacg ttgctgctgc    2700
cgccggtcgg gcagccgacc gcgcagttgt cgatggattc gagcgtgtcg gccgacgcct    2760
gcgcggcgaa cagcagggcg gccaaggcca acatcttgtt gttaaagcgc atatatatat    2820
ctccttttat ccacggtcag aagtgaccag ttcgttcttc tcccaccaac gcttaaggtc    2880
gaacgaaggg caagccttcg gcgccacctc atgatgggcg cgaagaccag cgccttcgta    2940
cttagccagc agtgtgacaa gcagtgagcg aagggattgc atttgggctg cgctaaagtt    3000
agcgtcgaac ttacctttat cgtcgatacc accaacaagg cagacgccga tagagttgtg    3060
gttgtaaccc ttagcgtgag agcctacagc catctcatct cgtcctgcct ccacagtacc    3120
gtctcgcttg atgataaagt ggtatcccac atcgagccaa ccctgctctt tgtgccactg    3180
gcgaatctca cggacaccaa cattctgact tggcttggta gccgagcagt gaacaaagat    3240
tgcgtcagta gattcacgtt gtttaaactg tacacgagcc attatttctt tcctcctttc    3300 cttttttaatc tatcaaaggg gacccggatc ctctacgccg gacgcatcgt ggccggcatc    3360
accggcgcca caggtgcggt tgctggcgcc tatatcgccg acatcaccga tggggaagat    3420
cgggctcgcc acttcgggct catgagcgct tgtttcggcg tgggtatggt ggcaggcccc    3480
gtggccgggg gactgttggg cgccatctcc ttgcatgccg atcgtcagcc tgtcgactgc    3540
agtctagcac tagtcgcgag gtaccattcc gacaccatcg aatggtgcaa aacctttcgc    3600
ggtatggcat gatagcgccc ggaagagagt caattcaggg tggtgaatgt gaaaccagta    3660
acgttatacg atgtcgcaga gtatgccggt gtctcttatc agaccgtttc ccgcgtggtg    3720
aaccaggcca gccacgtttc tgcgaaaacg cgggaaaaag tggaagcggc gatggcggag    3780
ctgaattaca ttcccaaccg cgtggcacaa caactggcgg caaacagtc gttgctgatt    3840 ggcgttgcca cctccagtct ggccctgcac gcgccgtcgc aaattgtcgc ggcgattaaa    3900
tctcgcgccg atcaactggg tgccagcgtg gtggtgtcga tggtagaacg aagcggcgtc    3960
gaagcctgta aagcggcggt gcacaatctt ctcgcgcaac gcgtcagtgg gctgatcatt    4020
aactatccgc tggatgacca ggatgccatt gctgtggaag ctgcctgcac taatgttccg    4080
```

```
gcgttatttc ttgatgtctc tgaccagaca cccatcaaca gtattatttt ctcccatgaa      4140
gacggtacgc gactgggcgt ggagcatctg gtcgcattgg gtcaccagca aatcgcgctg      4200
ttagcgggcc cattaagttc tgtctcggcg cgtctgcgtc tggctggctg gcataaatat      4260
ctcactcgca atcaaattca gccgatagcg aacgggaag gcgactggag tgccatgtcc       4320
ggttttcaac aaaccatgca aatgctgaat gagggcatcg ttcccactgc gatgctggtt      4380
gccaacgatc agatggcgct gggcgcaatg cgcgccatta ccgagtccgg gctgcgcgtt      4440
ggtgcggata tctcggtagt gggatacgac gataccgaag acagctcatg ttatatcccg      4500
ccgtcaacca ccatcaaaca ggattttcgc ctgctgggcg aaaccagcgt ggaccgcttg      4560
ctgcaactct ctcagggcca ggcggtgaag gcaatcagc tgttgcccgt ctcactggtg       4620
aaaagaaaaa ccaccctggc gcccaatacg caaaccgcct ctccccgcgc gttggccgat      4680
tcattaatgc agctggcacg acaggtttcc cgactggaaa gcgggcagtg agcgcaacgc      4740
aattaatgtg agttagctca ctcattaggc accggcgcgc ctagtcatat ggaagccggc      4800
ggcacctcgc taacggattc accactccaa gaattggagc caatcaattc ttgcggagaa      4860
ctgtgaatgc gcaaaccaac ccttggcaga acatatccat cgcgtccgcc atctccagca      4920
gccgcacgcg gcgcatctcg ggcagcgttg gtcctggcc acgggtgcgc atgatcgtgc       4980
tcctgtcgtt gaggacccgg ctaggctggc ggggttgcct tactggttag cagaatgaat      5040
caccgatacg cgagcgaacg tgaagcgact gctgctgcaa aacgtctgcg acctgagcaa      5100
caacatgaat ggtcttcggt ttccgtgttt cgtaaagtct ggaaacgcgg aagtcccta      5160 cgtgctgctg aagttgcccg caacagagag tggaaccaac cggtgatacc acgatactat      5220
gactgagagt caacgccatg agcggcctca tttcttattc tgagttacaa cagtccgcac      5280
cgctgtccgg tagctccttc cggtgggcgc ggggcatgac tatcgtcgcc gcacttatga      5340
ctgtcttctt tatcatgcaa ctcgtaggac aggtgccggc agcgcccaac agtccccgg      5400 ccacggggcc tgccaccata cccacgccga acaagcgcc ctgcaccatt atgttccgga      5460
tctgcatcgc aggatgctgc tggctaccct gtggaacacc tacatctgta ttaacgaagc      5520
gctaaccgtt tttatcaggc tctgggaggc agaataaatg atcatatcgt caattattac      5580
ctccacgggg agagcctgag caaactggcc tcaggcattt gagaagcaca cggtcacact      5640
gcttccggta gtcaataaac cggtaaacca gcaaatagaca taagcggcta tttaacgacc      5700
ctgccctgaa ccgacgaccg ggtcgaattt gctttcgaat ttctgccatt catccgctta      5760
ttatcactta ttcaggcgta gcaccaggcg tttaagggca ccaataactg ccttaaaaaa      5820
attacgcccc gccctgccac tcatcgcagt actgttgtaa ttcattaagc attctgccga      5880 catgaagcc atcacagacg gcatgatgaa cctgaatcgc cagcggcatc agcaccttgt       5940
cgccttgcgt ataatatttg cccatggtga aacgggggc gaagaagttg tccatattgg       6000
ccacgtttaa atcaaaactg gtgaaactca cccaggatt ggctgagacg aaaaacatat       6060
tctcaataaa ccctttaggg aaataggcca ggttttcacc gtaacacgcc acatcttgcg      6120
aatatatgtg tagaaactgc cggaaatcgt cgtggtattc actccagagc gatgaaaacg      6180
tttcagtttg ctcatggaaa acggtgtaac aagggtgaac actatcccat atcaccagct      6240
caccgtcttt cattgccata cg                                              6262
```

<210> SEQ ID NO 9
<211> LENGTH: 6031
<212> TYPE: DNA

<213> ORGANISM: Unknown
<220> FEATURE:
<223> OTHER INFORMATION: Artificial/synthetic sequence

<400> SEQUENCE: 9

```
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa agttggccc agggcttccc      360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gttttttgagg tgctccagtg gcttctgttt ctatcagctg tccctcctgt tcagctactg    540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggca aacccgaca ggactataaa gataccaggc gtttccctg gcggctccct       960
cgtgcgctct cctgttcctg cctttcggtt taccggtgtc attccgctgt tatggccgcg    1020
tttgtctcat tccacgcctg acactcagtt ccgggtaggc agttcgctcc aagctggact    1080
gtatgcacga accccccgtt cagtccgacc gctgcgcctt atccggtaac tatcgtcttg    1140
agtccaaccc ggaaagacat gcaaaagcac cactggcagc agccactggt aattgattta    1200
gaggagttag tcttgaagtc atgcgccggt taaggctaaa ctgaaaggac aagttttggt    1260
gactgcgctc ctccaagcca gttacctcgg ttcaaagagt tggtagctca gagaaccttc    1320
gaaaaaccgc cctgcaaggc ggttttttcg ttttcagagc aagagattac gcgcagacca    1380
aaacgatctc aagaagatca tcttattaat cagataaaat atttctagat tcagtgcaa     1440
tttatctctt caaatgtagc acctgaagtc agccccatac gatataagtt gtaattctca    1500
tgtttgacag cttatcatcg ataagcttta atgcggtagt ttatcacagt taaattgcta    1560
acgcagtcag gcaccgtgta tgaaatctaa caatgcgctc atcgtcatcc tcggcaccgt    1620
caccctggat gctgtaggca taggcttggt tatgccggta ctgccgggcc tcttgcggga    1680
tatcgtccat tccgacagca tcgccagtca ctatggcgtg ctgctagcgc tatatgcgtt    1740
gatgcaattt ctatgcgcac ccgttctcgg agcactgtcc gaccgctttg gccgccgccc    1800
agtcctgctc gcttcgctac ttggagccac tatcgactac gcgatcatgg cgaccacacc    1860
cgtcctgtgg atccggccca ttggctgcct cccacacttg gatatgcctc ctcggagcct    1920
tatagaattg tttataagac ttgcgcatta tttgacctcc aatgcgaaca aagggaaacc    1980
gctgtggtct cccttagtg agttcaatta attattgacc tgaatcagcg ttgtcttcgc     2040
tccaaatatt taatttctct tttttcgctt gtgcttcact ttttcttaaa tgttgttcat    2100
gtgtattgtt aggtttgtaa acataagcaa ctttagccaa gccttgacga actaaagctt    2160
cgtttaccat ttttccatca gcataaatat acgctaagcc acgtccatat ttatcagttc    2220
```

```
tttgaccttt gtcaaactcg acttcaattt tctttgcatt ttctaccatt tttttcgtaa    2280
atgcacttgc ttcaggacca tatttctcta cacctttttt aggatgcttt gtttcaggtg    2340
tatcaaccaa taatagtctg aatgtcattg gttgaccttt gtacattaat ttaaccgtat    2400
caccatcaat cgctttaatt aaagtcgcag gttcttatg taattttta gttgaagttg      2460 cactatatac tgttggatct tcagaaccac ttctatttac gccgttatct gtttggctgg    2520
cctgcgctac ggtagcgaaa ccagccagtg ccactgcaat cgcgatagct gtcttttca    2580 tatatatatc tccttttatc cacggtcaga agtgaccagt tcgttcttct cccaccaacg   2640
cttaaggtcg aacgaagggc aagccttcgg cgccacctca tgatgggcgc gaagaccagc    2700
gccttcgtac ttagccagca gtgtgacaag cagtgagcga agggattgca tttgggctgg    2760
cgtaaagtta gcgtcgaact tacctttatc gtcgatacca ccaacaaggc agacgccgat    2820
agagttgtgg ttgtaaccct tagcgtgaga gcctacagcc atctcatctc gtcctgcctc    2880
cacagtaccg tctcgcttga tgataaagtg gtatcccaca tcgagccaac cctgctcttt    2940
gtgccactgg cgaatctcac ggacaccaac attctgactt ggcttggtag ccgagcagtg    3000
aacaaagatt gcgtcagtag attcacgttg tttaaactgt acacgagcca ttatttcttt    3060
cctcctttcc tttttaatct atcaaagggg acccggatcc tctacgccgg acgcatcgtg    3120
gccggcatca ccggcgccac aggtgcggtt gctggcgcct atatcgccga catcaccgat    3180
ggggaagatc gggctcgcca cttcgggctc atgagcgctt gtttcggcgt gggtatggtg    3240
gcaggccccg tggccggggg actgttgggc gccatctcct tgcatgccga tcgtcagcct    3300
gtcgactgca gtctagcact agtcgcgagg taccattccg acaccatcga atggtgcaaa    3360
acctttcgcg gtatggcatg atagcgcccg gaagagagtc aattcagggt ggtgaatgtg    3420
aaaccagtaa cgttatacga tgtcgcagag tatgccggtg tctcttatca gaccgtttcc    3480
cgcgtggtga accaggccag ccacgtttct gcgaaaacgc gggaaaaagt ggaagcggcg    3540
atggcggagc tgaattacat tcccaaccgc gtggcacaac aactggcggg caaacagtcg    3600
ttgctgattg gcgttgccac ctccagtctg gccctgcacg cgccgtcgca aattgtcgcg    3660
gcgattaaat ctcgcgccga tcaactgggt gccagcgtgg tggtgtcgat ggtagaacga    3720
agcggcgtcg aagcctgtaa agcggcggtg cacaatcttc tcgcgcaacg cgtcagtggg    3780
ctgatcatta actatccgct ggatgaccag gatgccattg ctgtggaagc tgcctgcact    3840
aatgttccgg cgttatttct tgatgtctct gaccagacac ccatcaacag tattattttc    3900
tcccatgaag acggtacgcg actgggcgtg gagcatctgg tcgcattggg tcaccagcaa    3960
atcgcgctgt tagcgggccc attaagttct gtctcggcgc gtctgcgtct ggctggctgg    4020
cataaatatc tcactcgcaa tcaaattcag ccgatagcgg aacgggaagg cgactggagt    4080
gccatgtccg gttttcaaca aaccatgcaa atgctgaatg agggcatcgt tcccactgcg    4140
atgctggttg ccaacgatca gatggcgctg ggcgcaatgc gcgccattac cgagtccggg    4200
ctgcgcgttg gtgcggatat ctcggtagtg ggatacgacg ataccgaaga cagctcatgt    4260
tatatcccgc cgtcaaccac catcaaacag gattttcgcc tgctggggca aaccagcgtg    4320
gaccgcttgc tgcaactctc tcagggccag gcggtgaagg gcaatcagct gttgcccgtc    4380
tcactggtga aaagaaaaac caccctggcg cccaatacgc aaaccgcctc tccccgcgcg    4440
ttggccgatt cattaatgca gctggcacga caggttccc gactggaaag cgggcagtga    4500
gcgcaacgca attaatgtga gttagctcac tcattaggca ccggcgcgcc tagtcatatg    4560
```

```
-continued gaagccggcg gcacctcgct aacggattca ccactccaag aattggagcc aatcaattct    4620
tgcggagaac tgtgaatgcg caaaccaacc cttggcagaa catatccatc gcgtccgcca    4680
tctccagcag ccgcacgcgg cgcatctcgg gcagcgttgg gtcctggcca cgggtgcgca    4740
tgatcgtgct cctgtcgttg aggacccggc taggctggcg gggttgcctt actggttagc    4800
agaatgaatc accgatacgc gagcgaacgt gaagcgactg ctgctgcaaa acgtctgcga    4860
cctgagcaac aacatgaatg gtcttcggtt tccgtgtttc gtaaagtctg gaaacgcgga    4920
agtcccctac gtgctgctga agttgcccgc aacagagagt ggaaccaacc ggtgatacca    4980
cgatactatg actgagagtc aacgccatga gcggcctcat ttcttattct gagttacaac    5040
agtccgcacc gctgtccggt agctccttcc ggtgggcgcg gggcatgact atcgtcgccg    5100
cacttatgac tgtcttcttt atcatgcaac tcgtaggaca ggtgccggca gcgcccaaca    5160
gtcccccggc cacgggcct gccaccatac ccacgccgaa acaagcgccc tgcaccatta    5220
tgttccggat ctgcatcgca ggatgctgct ggctaccctg tggaacacct acatctgtat    5280
taacgaagcg ctaaccgttt ttatcaggct ctgggaggca gaataaatga tcatatcgtc    5340
aattattacc tccacgggga gagcctgagc aaactggcct caggcatttg agaagcacac    5400
ggtcacactg cttccggtag tcaataaacc ggtaaaccag caatagacat aagcggctat    5460
ttaacgaccc tgccctgaac cgacgaccgg gtcgaatttg ctttcgaatt tctgccattc    5520
atccgcttat tatcacttat tcaggcgtag caccaggcgt ttaagggcac caataactgc    5580
cttaaaaaaa ttacgccccg ccctgccact catcgcagta ctgttgtaat tcattaagca    5640
ttctgccgac atggaagcca tcacagacgg catgatgaac ctgaatcgcc agcggcatca    5700
gcaccttgtc gccttgcgta taatatttgc ccatggtgaa aacgggggcg aagaagttgt    5760
ccatattggc cacgtttaaa tcaaaactgg tgaaactcac ccaggattg gctgagacga    5820 aaaacatatt ctcaataaac cctttaggga aataggccag gttttcaccg taacacgcca    5880
catcttgcga atatatgtgt agaaactgcc ggaaatcgtc gtggtattca ctccagagcg    5940
atgaaaacgt ttcagtttgc tcatggaaaa cggtgtaaca agggtgaaca ctatcccata    6000
tcaccagctc accgtctttc attgccatac g                                  6031
```